(12) United States Patent
Lawton

(10) Patent No.: US 7,341,837 B2
(45) Date of Patent: Mar. 11, 2008

(54) SOLUBLE ANALYTE DETECTION AND AMPLIFICATION

(76) Inventor: Robert L. Lawton, 3 Burnham Rd., Gorham, ME (US) 04038

( * ) Notice: Subject to any disclaimer, the term of this patent is extended or adjusted under 35 U.S.C. 154(b) by 69 days.

(21) Appl. No.: 10/653,321

(22) Filed: Sep. 2, 2003

(65) Prior Publication Data

US 2005/0048500 A1   Mar. 3, 2005

(51) Int. Cl.
*C12Q 1/68* (2006.01)
*G01N 33/53* (2006.01)

(52) U.S. Cl. ............... 435/7.1; 435/6; 435/91.1; 435/91.2; 435/971; 435/973

(58) Field of Classification Search ............ 435/6, 435/7.1, 174, 283.1; 422/50, 68.1, 82.05
See application file for complete search history.

(56) References Cited

U.S. PATENT DOCUMENTS

| | | | |
|---|---|---|---|
| 4,134,792 A * | 1/1979 | Boguslaski et al. ............ 435/4 |
| 5,244,816 A * | 9/1993 | Subramanian ............... 436/545 |
| 5,648,213 A * | 7/1997 | Reddy et al. ................... 435/6 |
| 5,705,338 A * | 1/1998 | Piran et al. ..................... 435/6 |
| 6,511,809 B2 * | 1/2003 | Baez et al. ..................... 435/6 |
| 6,686,150 B1 * | 2/2004 | Blackburn et al. ............. 435/6 |
| 6,797,481 B1 * | 9/2004 | Ullman et al. ............... 435/7.1 |

OTHER PUBLICATIONS

Hendrickson et al "High sensitivity multianalyte immunoassay using covalent DNA-labeled antibodies and polymerase chain reaction" Nucleic Acids Research, 1995, 522-529.*

* cited by examiner

*Primary Examiner*—David A. Saunders
(74) *Attorney, Agent, or Firm*—T D Foster; M. Reza Savari

(57) ABSTRACT

The present invention relates to a method of detection of a compound of interest that is present at low levels in a sample. In particular, the present invention relates to a method of detection of a compound of interest in solution by a nucleic acid-labelled binding construct, separation of the unbound nucleic acid-labelled binding construct, and the detection of the bound nucleic acid-labelled binding construct in the solution phase. The present invention is particularly adaptable to be used in conjunction with a nucleic acid amplification reaction for detecting the presence or absence of the nucleic acid portion of binding construct in a sample indicating the presence or absence of the compound of interest.

32 Claims, 6 Drawing Sheets

| | |
|---|---|
| 1 | Molecular weight standards |
| 2 | pUC19 control |
| 3 | 790 picograms |
| 4 | 395 picograms |
| 5 | 198 picograms |
| 6 | 98 picograms |
| 7 | 49 picograms |
| 8 | 24 picograms |
| 9 | 12 picograms |
| 10 | Positive Control |
| 11 | Negative Control |
| 12 | H$_2$O |

SOLUBLE ANALYTE DETECTION AND AMPLIFICATION

FIELD OF INVENTION

The present invention relates generally to the field of compound detection, and particularly to methods for compound detection and a kit for compound detection.

BACKGROUND OF THE INVENTION

The detection of immune responses to pathological organisms or the detection of pathogen-related proteins or other antigens in the serum of patients has benefited greatly from immunoassay development over the last 15 years. In one form of immunoassay, monoclonal or polyclonal antibodies that recognize the immunoglobulins of another species are used. These reagents, known as anti-species antibodies are labelled, typically with a fluorochrome or enzyme, and used to detect antigen binding by immunoglobulins found in immune serum. In another form of immunoassay, known as the sandwich assay, antibodies directed against pathogen proteins are used to capture antigen from, for example, patients' serum or cerebrospinal fluid (CSF), that is then detected by the binding of another, labelled antibody directed against the same antigen. All of these assays, however, are limited by the sensitivity of detection of the bound immunoglobulin and require fairly large concentrations, on a molar basis, of labelled reagent.

More recent assays utilize nucleic acid amplification methods, such as the polymerase chain reaction (PCR) for DNA amplification, to detect very low levels of nucleic acid. Nucleic acid amplification methods can allow the detection of pathological agents in serum or in the environment at levels well below that of immunoassay detection. Such techniques, however, are often very sensitive to contamination from the environment and require prior knowledge of the nucleic acid sequence of interest in order to identify a portion of the nucleic acid and amplify it for detection. Nucleic acid amplification requires that there be nucleic acid present to amplify and detect and is, therefore, of no or limited utility when the compound of interest is a protein, carbohydrate, or other non-nucleic acid molecule. Further improvements in the effectiveness and sensitivity of compound detection in a sample are desirable, and the present invention addresses the existing problems and provides related benefits.

SUMMARY OF THE INVENTION

Throughout this application various publications are referenced. The disclosures of these publications are hereby incorporated by reference, in their entirety, in this application. Citations of these documents are not intended as an admission that any of them are pertinent prior art. All statements as to the date or representation as to the contents of these documents is based on the information available to the applicant and does not constitute any admission as to the correctness of the dates or contents of these documents.

The present invention relates to a method of detection of a compound of interest that can be present at low levels in a sample. In particular, the present invention relates to a method of detection of a compound of interest in solution by a nucleic acid-labelled binding construct that binds the compound of interest, separation of the unbound nucleic acid-labelled binding construct, and the detection of the bound nucleic acid-labelled binding construct in the solution phase. The present invention is particularly adaptable to be used in conjunction with a nucleic acid amplification method for detecting the presence or absence of the nucleic acid portion of the binding construct in a sample, thus indicating the presence or absence of the compound of interest.

The present invention recognizes that compound detection methods can be made more sensitive and thereby more effective by separation from the solution any excess or unbound binding construct that is not bound to the compound of interest, thus increasing the proportion of true "positive" signal to false "positive" signal. The present invention further provides a versatile detection system that does not require solid-phase capture or detection of the compound of interest. Where the compound of interest includes a non-nucleic acid molecule such as a peptide or protein, a method of the present invention further provides the advantage of not requiring prior knowledge of the nucleic acid sequence encoding the peptide or protein of interest in order to identify it and to use DNA amplification for its detection.

A first aspect of the present invention is a method for detecting a compound of interest in a sample, including the use of a binding construct. The binding construct includes a recognition portion which recognizes and binds the compound of interest, and a nucleic acid portion. When the binding construct is mixed with the sample, the recognition portion binds with the compound of interest and forms construct-compound complexes. The present invention also includes surfaces bearing one or more accessible binding targets capable of binding to the recognition portion of the binding construct. When the surfaces are contacted with the mixture of the sample and binding construct, the accessible binding targets of the surfaces bind with any excess or unbound binding construct to form construct-surface complexes. After sufficient incubation, the construct-surface complexes and any unbound or excess surfaces are separated from the mixture leaving behind the construct-compound complexes in solution. After separation, the solution is analysed in order to detect the presence or absence of the nucleic acid portion of the binding construct, wherein the presence of the nucleic acid portion of the binding construct indicates the presence of the compound of interest in the sample.

A second aspect of the present invention is a method for increasing the sensitivity of solution-phase detection of a compound of interest in a sample. The method includes providing a sample suspected of containing the compound of interest; providing a binding construct including a recognition portion capable of binding the compound of interest, and a nucleic acid portion; and contacting the sample with the binding construct for a period of time sufficient to permit the recognition portion to bind any compound of interest in the sample, thus forming construct-compound complexes in solution. The method further includes providing one or more surfaces that bears one or more accessible binding target capable of binding to the recognition portion, and contacting the surface with the solution for a period of time sufficient for the accessible binding target to bind the recognition portion of any binding construct not bound to the compound of interest, thereby forming construct-surface complexes. The construct-surface complexes are separated from the solution, leaving the construct-compound complexes in the solution. The presence or absence of the nucleic acid portion of the binding construct is detected in the solution. The separation of the construct-surface complexes from the solution results in a separation of substantially all binding constructs not bound to a compound of interest and in an increased sensitivity of detection of the compound of interest, and the presence of the nucleic acid portion of the binding construct indicates the presence of the compound of interest in the sample.

A third aspect of the present invention is a kit for detecting a compound of interest including a binding construct comprising a recognition portion which recognizes and binds the compound of interest, and a nucleic acid portion. The kit of the present invention also includes one or more surfaces bearing one or more accessible binding targets capable of binding to the recognition portion of the binding construct. The kit of the present invention can also optionally include a nucleic acid amplification primer pair, wherein each primer of the primer pair hybridizes to its complementary sequence at the 3' end of a target nucleic acid sequence of the nucleic acid portion of the binding construct.

DETAILED DESCRIPTION OF THE INVENTION

Introduction

Figure 1:
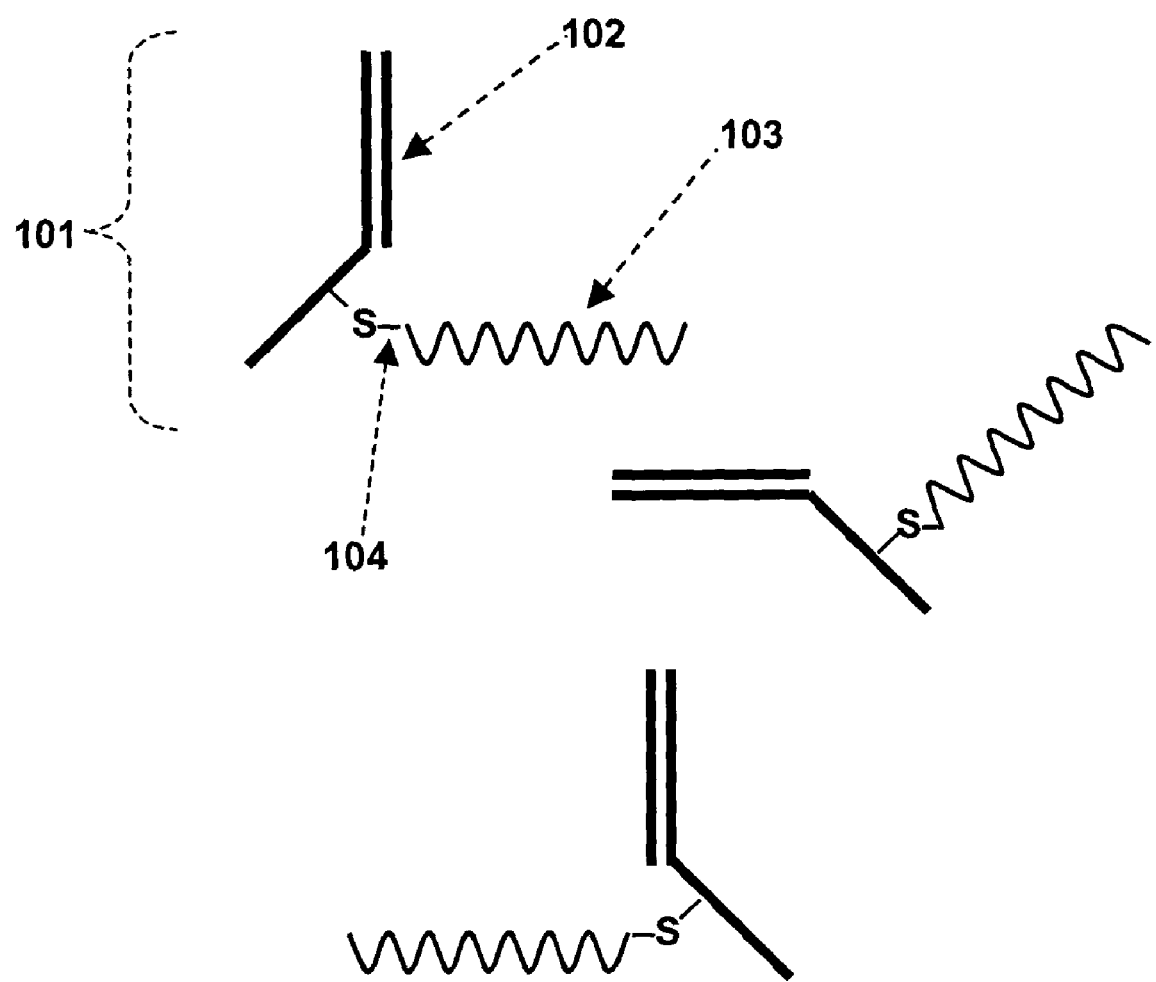
FIG. 1 depicts a plurality of binding constructs, each including a recognition portion and a nucleic acid portion (see Example I).

The present invention recognizes that compound detection methods can be made more sensitive and thereby more effective by increasing the proportion of true "positive" signal to false "positive signal". The present invention further recognizes the versatility of a detection system that does not require solid-phase detection of the compound of interest, and further recognizes the desirability of benefiting from signal amplification methods (such as nucleic acid amplification) even in the detection of a compound of interest that does not include a nucleic acid.

As a non-limiting introduction to the breadth of the present invention, the present invention includes several general and useful aspects, including:

1) A method for detecting a compound of interest in a sample, including the steps of: providing a binding construct including a recognition portion which recognizes and binds the compound of interest, and a nucleic acid portion; mixing the binding construct with the sample to form construct-compound complexes; providing one or more surface, wherein the surface bears one or more accessible binding targets capable of recognizing and binding to the recognition portion of the binding construct; introducing the surface to the mixture of the binding construct and the sample in order for the surface to form construct-surface complexes with any unbound binding constructs; separating the construct-surface complexes from the mixture leaving behind the construct-compound complexes; detecting the presence or absence of the nucleic acid portion of the binding construct, wherein the presence of the nucleic acid portion of the binding construct indicates the presence of the compound of interest in the sample.

2) A method for increasing the sensitivity of solution-phase detection of a compound of interest, including the steps of: providing a sample suspected of containing the compound of interest; providing a binding construct that includes a recognition portion capable of binding the compound of interest, and a nucleic acid portion; contacting the sample with the binding construct for a period of time sufficient to permit the recognition portion to bind any compound of interest in the sample, thus forming construct-compound complexes in solution; providing one or more surfaces that bears one or more accessible binding target capable of binding to the recognition portion; contacting the surface with the solution for a period of time sufficient for the accessible binding target to bind the recognition portion of any binding construct not bound to the compound of interest, thereby forming construct-surface complexes; separating the construct-surface complexes from the solution, leaving the construct-compound complexes in the solution; and detecting the presence or absence of the nucleic acid portion of the binding construct in the solution, wherein the separation of the construct-surface complexes from the solution results in a separation of substantially all binding constructs not bound to a compound of interest and in an increased sensitivity of detection of the compound of interest, and wherein the presence of the nucleic acid portion of the binding construct indicates the presence of the compound of interest in the sample.

3) A kit for detecting a compound of interest comprising: a binding construct comprising a recognition portion which recognizes and binds the compound of interest, and a nucleic acid portion; and one or more surfaces, wherein the surfaces bear one or more accessible binding targets known to be capable of binding to the recognition portion of the binding construct. The kit includes, optionally, a nucleic acid primer pair, wherein the wherein each primer of the primer pair hybridizes to its complementary sequence at the 3' end of a target nucleic acid sequence of the nucleic acid portion of the binding construct.

The present invention relates to a sensitive method for the detection of a compound of interest present in a sample, such as a biological fluid, a biological extract, or an environmental sample, by means of a nucleic acid-labelled binding construct which is capable of recognizing and binding the compound of interest. This compound detection method is called soluble analyte detection and amplification. The present invention provides a method for detection of a compound of interest that is particularly adaptable for use with samples wherein the compound of interest is present in the sample in low levels. "Sensitivity" can be defined as the proportion of true positives detected by a system designed to discriminate between two categories, known conventionally as positive and negative. The present invention provides enhanced detection sensitivity because it is possible to provide even excess amounts of the binding construct, and then separate from the sample any unbound (that is to say, not bound to a compound of interest) or excess binding construct (detection of which would lead to a false "positive" signal), thus leaving in solution only the binding construct that is bound to a compound of interest in a construct-compound complex available for detection as a true "positive" signal. Thus, detection sensitivity is proportional to the efficiency of separation of unbound or excess binding construct from the solution. The present invention is also generally more versatile because detection occurs in the solution phase and is not restricted to solid phase detection. Furthermore, only one binding entity (the binding construct) is required to recognize and bind the compound of interest, thus avoiding the problems associated with methods using two binding entities, for example, the problems of steric hindrance or potential loss of sensitivity from conformational changes induced by the binding of a first antibody, such as may occur for example, in a two-antibody sandwich assay.

Further objectives and advantages of the present invention will become apparent as the description proceeds and when taken in conjunction with the accompanying drawings. To gain a full appreciation of the scope of the present invention, it will be further recognized that various aspects of the present invention can be combined to make desirable embodiments of the invention.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. The technical terms used herein have their ordinary meaning in the art that they are used, as exemplified by a variety of technical dictionaries. Where a term is provided in the singular, the inventor also contemplates the plural of that term. The nomenclature used herein and the procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries (for example, Chambers Dictionary of Science and Technology, Peter M. B. Walker (editor), Chambers Harrap Publishers, Ltd., Edinburgh, UK, 1999, 1325 pp.). The inventors do not intend to be limited to a mechanism or mode of action. Reference thereto is provided for illustrative purposes only.

I. Method for Detecting a Compound of Interest in a Sample

The first method of the present invention includes a sensitive method for detection of a compound of interest in a sample that is capable of detecting the presence of very low quantities of the compound of interest in the sample. The first method of the present invention involves the recognition of a compound of interest by a nucleic acid-labelled binding construct, separation of the unbound nucleic acid-labelled binding construct by means of one or more surfaces bearing one or more binding targets, and detecting in solution the presence or absence of the nucleic acid portion of the binding construct wherein the presence of the nucleic acid portion of the binding construct indicates the presence of the compound of interest in the sample. The sample suspected of containing the compound of interest may be, for example, of entirely natural origin, of entirely non-natural origin (such as of synthetic origin), or a combination of natural and non-natural origins. The sample may include whole cells, tissues, organs, biological fluids, extracts, or environmental samples.

The first method of the present invention includes use of a binding construct. The binding constructs are mixed with the sample, allowing the recognition portion of the binding construct to bind to the compound of interest to form construct-compound complexes in solution.

The binding construct includes a recognition portion that can recognize and bind to the compound of interest, and a nucleic acid portion. The recognition portion can include virtually any molecule or combination of molecules capable of recognizing and binding the compound of interest. Such recognition portions can include, without limitation, peptides, polypeptides, antibodies, Fab fragments, nucleic acids, nucleic acid mimics, cell surface antigens, carbohydrates, or combination thereof. In one embodiment, the recognition portion includes an antibody (natural, modified, or recombinant) or an antibody fragment (such as an Fab fragment or single-chain antibody variable region fragment). In other embodiments, the recognition portion can be an antigen that binds an antibody, an aptamer that binds a target such as a peptide or small molecule, or a receptor that binds a ligand. In one preferred embodiment, the recognition portion binds monovalently to the compound of interest. In another preferred embodiment, the recognition portion binds multivalently, for example bivalently and optionally bispecifically, to the compound of interest.

The nucleic acid portion of the binding construct can include any nucleic acid or nucleic acid mimic that is capable of being detected. The nucleic acid that is used as the nucleic acid portion of the binding construct can include any type of nucleic acid, for example DNA or RNA, or a nucleic acid mimic (such as, but not limited to, a peptide nucleic acid), or a combination thereof. The nucleic acid of the invention can be single-stranded or double-stranded. In one preferred embodiment, the binding construct of the present invention includes a nucleic acid portion, wherein the sequence of the nucleic acid portion does not include a sequence that is expected to be found in the sample, and can thereby be reasonably expected to be less easily contaminated by nucleic acid sequences in the sample, but is, however, designed so as to be easily detectable. The nucleic acid portion is preferably sufficiently long enough to be easily detectable by the detection method chosen.

The recognition portion can be attached to the nucleic acid portion by any method, covalently or non-covalently, directly or indirectly, and it will depend on the nature of a given recognition portion. Non-covalent attachment methods include but are not limited to physical adsorption, electrostatic forces, ionic interactions, hydrogen bonding, hydrophilic-hydrophobic interactions, van der Waals forces, and magnetic forces. Where desired, for example, when increased flexibility is needed, a recognition portion may be indirectly affixed to the nucleic acid portion using a spacer arm. Preferably, the recognition portion is attached to the nucleic acid portion via covalent linkage, or via a high affinity non-covalent interaction such as that of biotin and avidin.

The first method of the present invention includes the use of one or more surfaces that bears one or more accessible binding targets that are known to be recognized by and bind to the recognition portion of the binding construct. Such surfaces can be any particle capable of being separated from a liquid sample, or such surfaces may be non-particulate surfaces such as planar or non-planar surfaces, or a combination thereof. The surfaces can be optionally enclosed, for example, in a chamber. The binding targets can include any target capable of being recognized by and binding to the recognition portion of the binding construct, for example, peptide mimotopes or epitope mimetics for antibody variable regions, whole or partial antigen, nucleic acids, or sugar moieties. The accessible binding target can be attached to the surface by any method, and it will depend on the nature of a given surface and binding target.

When the surfaces are introduced to the mixture of the sample and binding construct, after sufficient incubation, the accessible binding targets of the surfaces bind any unbound recognition portions of the binding construct forming construct-surface complexes. The construct-surface and any excess unbound surfaces are then separated from the construct-compound complexes in solution in the sample, by methods suitable to the type of surface used, for example, a magnet to separate magnetic particles, decanting from a planar surface, or separation by pressure or vacuum, centrifugation, or filtration. Alternatively, any binding construct not bound to a compound of interest in a construct-compound complex can be separated from solution by methods such as, but not limited to, precipitation, "salting-out", size-exclusion or filtration, extraction, or phase-separation.

After the separation step, by detecting the presence or absence of the nucleic acid portion of the binding construct, the presence or absence of the compound of interest in the sample is determined. The presence or absence of the nucleic acid portion of the binding construct can be detected by any method that is capable of detecting the presence or absence of nucleic acid, for example, enzymatic amplification, hybridization, or detection of a label. In one embodiment of the present invention, the method can be preferably adapted to detect the presence or absence of the nucleic acid portion of the binding construct by amplification of the nucleic acid portion, for example, by means of a polymerase chain reaction with appropriate primers. In this embodiment, only a few, and at least only one, construct-compound complex needs to serve as a template for nucleic acid amplification. The amplified nucleic acid can be measured or detected by any suitable method, for example, using labelled oligonucleotides or by detecting appropriate bands on polyacrylamide gel electrophoresis.

In one embodiment of the present invention, the sample to be analyzed may contain two or more compounds of interest. In order to detect two or more different compounds of interest in a sample, two or more different types of binding constructs, each having a different recognition portion capable of recognizing a different compound, are provided. Each type of binding construct includes a nucleic acid portion unique to the type, in order to detect the presence or absence of two or more compounds of interest in the sample.

II. Method from Increasing the Sensitivity of Solution-Phase Detection of a Compound of Interest The second method of the present invention includes a method for increasing the sensitivity of solution-phase detection of a compound of interest. The method is especially suitable for samples that are suspected to contain a low concentration or low quantities of the compound of interest.

The second method of the present invention includes the steps of: providing a sample suspected of containing the compound of interest; providing a binding construct that includes a recognition portion capable of binding the compound of interest, and a nucleic acid portion; contacting the sample with the binding construct for a period of time sufficient to permit the recognition portion to bind any compound of interest in the sample, thus forming construct-compound complexes in solution; providing one or more surfaces that bears one or more accessible binding target capable of binding to the recognition portion; contacting the surface with the solution for a period of time sufficient for the accessible binding target to bind the recognition portion of any binding construct not bound to the compound of interest, thereby forming construct-surface complexes; separating the construct-surface complexes from the solution, leaving the construct-compound complexes in the solution; and detecting the presence or absence of the nucleic acid portion of the binding construct in the solution, wherein the separation of the construct-surface complexes from the solution results in a separation of substantially all binding constructs not bound to a compound of interest and in an increased sensitivity of detection of the compound of interest, and wherein the presence of the nucleic acid portion of the binding construct indicates the presence of the compound of interest in the sample.

The second method of the present invention includes the steps of providing a sample suspected of containing a compound of interest, and providing a binding construct. The sample suspected of containing the compound of interest may be, for example, of entirely natural origin, of entirely non-natural origin (such as of synthetic origin), or a combination of natural and non-natural origins. The sample may include whole cells, tissues, organs, biological fluids, extracts, or environmental samples. The binding construct includes a recognition portion that can recognize and bind to the compound of interest, and a nucleic acid portion. The sample is contacted with the binding construct for a period of time sufficient to permit the recognition portion of the binding construct to bind the compound of interest and form a construct-compound complex in solution.

The recognition portion of the binding construct can include virtually any molecule or combination of molecules capable of recognizing and binding the compound of interest. Such recognition portions can include, without limitation, peptides, polypeptides, antibodies, Fab fragments, nucleic acids, nucleic acid mimics, cell surface antigens, carbohydrates, or combination thereof. In one embodiment, the recognition portion includes an antibody (natural, modified, or recombinant) or an antibody fragment (such as an Fab fragment or single-chain antibody variable region fragment). In other embodiments, the recognition portion can be an antigen that binds an antibody, an aptamer that binds a target such as a peptide or small molecule, or a receptor that binds a ligand. In one preferred embodiment, the recognition portion binds monovalently to the compound of interest. In another preferred embodiment, the recognition portion binds multivalently, for example bivalently and optionally bispecifically, to the compound of interest.

The nucleic acid portion of the binding construct can include any nucleic acid or nucleic acid mimic that is capable of being detected. The nucleic acid that is used as the nucleic acid portion of the binding construct can include any type of nucleic acid, for example DNA or RNA, or a nucleic acid mimic (such as, but not limited to, a peptide nucleic acid), or a combination thereof. The nucleic acid of the invention can be single-stranded or double-stranded. In one preferred embodiment, the binding construct of the present invention includes a nucleic acid portion, wherein the sequence of the nucleic acid portion does not include a sequence that is expected to be found in the sample, and can thereby be reasonably expected to be less easily contaminated by nucleic acid sequences in the sample, but is, however, designed so as to be easily detectable. The nucleic acid portion is preferably sufficiently long enough to be easily detectable by the detection method chosen.

The recognition portion can be attached to the nucleic acid portion by any method, covalently or non-covalently, directly or indirectly, and it will depend on the nature of a given recognition portion. Non-covalent attachment methods include but are not limited to physical adsorption, electrostatic forces, ionic interactions, hydrogen bonding, hydrophilic-hydrophobic interactions, van der Waals forces, and magnetic forces. Where desired, for example, when increased flexibility is needed, a recognition portion may be indirectly affixed to the nucleic acid portion using a spacer arm. Preferably, the recognition portion is attached to the nucleic acid portion via covalent linkage, or via a high affinity non-covalent interaction such as that of biotin and avidin.

The second method of the present invention includes providing one or more surfaces bearing one or more accessible binding targets that are known to be recognized by and bind to the recognition portion of the binding construct. Such surfaces can be any particle capable of being separated from a liquid sample, or such surfaces may be non-particulate surfaces such as planar or non-planar surfaces, or a combination thereof. The surfaces can be optionally enclosed, for example, enclosed in a chamber. The binding targets can include any target capable of being recognized by and binding to the recognition portion of the binding construct, for example, peptide mimotopes or epitope mimetics for antibody variable regions, whole or partial antigen, nucleic acids, or sugar moieties. The accessible binding target can be attached to the surface by any method, and it will depend on the nature of a given surface and binding target.

The surfaces are contacted with the solution for a period of time sufficient for the accessible binding target to bind the recognition portion of any binding construct not bound to a compound of interest, thus forming construct-surface complexes. The construct-surface complexes and any excess unbound surfaces are separated from the solution, leaving behind the construct-compound complexes. Separation may be by any method suitable to the type of surface used, for example, a magnet to separate magnetic particles, decanting from a planar surface, or separation by pressure or vacuum, centrifugation, or filtration. Alternatively, any binding construct not bound to a compound of interest in a construct-compound complex can be separated from solution by methods such as, but not limited to, precipitation, "salting-out", size-exclusion or filtration, extraction, or phase-separation. Separation of the construct-surface complexes and any excess unbound surfaces results in a separation of substantially all binding constructs not bound to a compound of interest. Most preferably, all binding constructs not bound to a compound of interest are separated from solution. Separation of the construct-surface complexes and any excess unbound surfaces results in a decrease in "false" positive signal generated by binding complexes not bound to a compound of interest, and thus in an increased sensitivity of detection of the compound of interest relative to an assay wherein unbound or excess binding constructs is not separated.

After the separation step, by detecting the presence or absence of the nucleic acid portion of the binding construct, the presence or absence of the compound of interest in the sample is determined. The presence or absence of the nucleic acid portion of the binding construct can be detected by any method that is capable of detecting the presence or absence of nucleic acid, for example, enzymatic amplification, hybridization, or detection of a label. In one embodiment of the present invention, the method can be preferably adapted to detect the presence or absence of the nucleic acid portion of the binding construct by amplification of the nucleic acid portion, for example, by means of a polymerase chain reaction with appropriate primers. In this embodiment, only a few, and at least only one, construct-compound complex needs to serve as a template for nucleic acid amplification. The amplified nucleic acid can be measured or detected by any suitable method, for example, using labelled oligonucleotides or by detecting appropriate bands on polyacrylamide gel electrophoresis.

In one embodiment of the present invention, the sample to be analyzed may contain two or more compounds of interest. In order to detect two or more different compounds of interest in a sample, two or more different types of binding constructs, each having a different recognition portion capable of recognizing a different compound, are provided. Each type of binding construct includes a nucleic acid portion unique to the type, in order to detect the presence or absence of two or more compounds of interest in the sample.

III. Kit for Detection of a Compound of Interest

The present invention also includes a kit used for the detection of a compound of interest in a sample that is capable of detecting the presence of very low quantities of the compound of interest in the sample.

The kit of the present invention includes a binding construct. The binding construct includes a recognition portion that can recognize and bind to the compound of interest, and a nucleic acid portion. The recognition portion can include virtually any molecule or combination of molecules capable of recognizing and binding the compound of interest. Such recognition portions can include, without limitation, peptides, polypeptides, antibodies, Fab fragments, nucleic acids, nucleic acid mimics, cell surface antigens, carbohydrates, or combination thereof. In one embodiment, the recognition portion includes an antibody (natural, modified, or recombinant) or an antibody fragment (such as an Fab fragment or single-chain antibody variable region fragment). In other embodiments, the recognition portion can be an antigen that binds an antibody, an aptamer that binds a target such as a peptide or small molecule, or a receptor that binds a ligand. In one preferred embodiment, the recognition portion binds monovalently to the compound of interest. In another preferred embodiment, the recognition portion binds multivalently, for example bivalently and optionally bispecifically, to the compound of interest.

The nucleic acid portion of the binding construct can include any nucleic acid or nucleic acid mimic that is capable of being detected. The nucleic acid that is used as the nucleic acid portion of the binding construct can include any type of nucleic acid, for example DNA or RNA, or a nucleic acid mimic (such as, but not limited to, a peptide nucleic acid), or a combination thereof. The nucleic acid of the invention can be single-stranded or double-stranded. In one preferred embodiment, the binding construct of the present invention includes a nucleic acid portion, wherein the sequence of the nucleic acid portion does not include a sequence that is expected to be found in the sample, and can thereby be reasonably expected to be less easily contaminated by nucleic acid sequences in the sample, but is, however, designed so as to be easily detectable. The nucleic acid portion is preferably sufficiently long enough to be easily detectable by the detection method chosen.

The recognition portion can be attached to the nucleic acid portion by any method, covalently or non-covalently, directly or indirectly, and it will depend on the nature of a given recognition portion. Non-covalent attachment methods include but are not limited to physical adsorption, electrostatic forces, ionic interactions, hydrogen bonding, hydrophilic-hydrophobic interactions, van der Waals forces, and magnetic forces. Where desired, for example, when increased flexibility is needed, a recognition portion may be indirectly affixed to the nucleic acid portion using a spacer arm. Preferably, the recognition portion is attached to the nucleic acid portion via covalent linkage, or via a high affinity non-covalent interaction such as that of biotin and avidin.

The kit of the present invention also includes one or more surfaces that bears one or more accessible binding targets that are known to be recognized by and bind to the recognition portion of the binding construct. Such surfaces can be any particle capable of being separated from a liquid sample, or such surfaces may be non-particulate surfaces such as planar or non-planar surfaces, or a combination thereof. The surfaces can be optionally enclosed, for example, in a chamber. The binding targets can include any target capable of being recognized by and binding to the recognition portion of the binding construct, for example, peptide mimotopes or epitope mimetics for antibody variable regions, whole or partial antigen, nucleic acids, or sugar moieties. The accessible binding target can be attached to the surface by any method, and it will depend on the nature of a given surface and binding target.

In embodiments wherein the nucleic acid portion of the binding construct is detected by nucleic acid amplification, the kit can optionally include a nucleic acid amplification primer pair, for example, a PCR primer pair wherein each primer of the primer pair hybridizes to its complementary sequence at the 3' end of a target nucleic acid sequence of the nucleic acid portion. The kit can further optionally include enzymes for nucleic acid amplification, such as Taq polymerase or RNA reverse transcriptase. In embodiments wherein the nucleic acid portion of the binding construct is detected by nucleic acid hybridization, the kit may contain one or more hybridization probes, such as oligonucleotides labelled with a detectable label. In embodiments including amplification of a signal, the kit may optionally include the reagents needed for signal amplification, such as enzymes or substrates. Kits of the invention can optionally include reagents for direct detection of the nucleic acid portion of the binding construct, such as molecular beacons or an appropriate antibody. The kit can optionally include means for separation of construct-surface complexes and any unbound surfaces, for example a magnet for embodiments wherein the surface is a magnetic particle, a filter for embodiments wherein the surface is a filterable particulate, or a pipette for embodiments wherein the surface is the walls of a tube.

Optionally, the kit can include instructions for the use of the kit. Such instructions may be in any suitable form, such as a brochure, leaflet, pamphlet, booklet, or audiovisual materials. Preferably the instructions are sufficiently detailed to permit a user of the kit to successfully use the kit to detect a compound of interest in a sample. Such instructions may include, for example, instructions for mixing reagents, manipulating components of the kit, proper handling of a sample, guidance in safety measures and in interpreting results, and trouble-shooting instructions.

The Compound of Interest

The methods and kits of the present invention may be used to detect various classes of compounds of interest. The methods are particularly suitable to the detection of compounds of interest that are suspected to be present in low amounts or low concentrations in a sample. Compounds of interest can include, but are not limited to, nucleic acids, peptides, proteins, glycoproteins, lipoproteins, lectins, antibodies, enzymes, and receptors; carbohydrates (monosaccharides, oligosaccharides, and polysaccharides) and glycosylated molecules; lipids, fats, and lipidated molecules; and whole or partial antigens. Compounds of interest may be small molecules (for example, ligands for a receptor, drugs of abuse, inorganic ions, metals, or chelates, metabolites, chemical intermediates, or natural products). Compounds of interest may be monomers, oligomers, or polymers; they can also be multi-molecular assemblies (for example, amyloid beta protofibrils, the dystrophin-glycoprotein assembly, proteosomes, chaperone proteins, or fragments of cell walls or cell membranes). Compounds of interest may be of completely natural origin, completely artificial origin, or a combination of both (such as a compound of natural origin that is chemically or physically modified).

The Sample

The methods of the invention may be applied to any suitable sample that is suspected of containing the compound of interest. The sample may be of entirely natural origin, of entirely non-natural origin (such as of synthetic origin), or a combination of natural and non-natural origins. A sample may include whole cells (such as prokaryotic cells, bacterial cells, eukaryotic cells, plant cells, fungal cells, or cells from multi-cellular organisms including invertebrates, vertebrates, mammals, and humans), tissues, organs, or biological fluids (such as, but not limited to, blood, serum, plasma, urine, semen, and cerebrospinal fluid). A sample may be an extract made from biological materials, such as from prokaryotes, bacteria, eukaryotes, plants, fungi, multicellular organisms or animals, invertebrates, vertebrates, mammals, non-human mammals, and humans. A sample may be an extract made from whole organisms or portions of organisms, cells, organs, tissues, fluids, whole cultures or portions of cultures, or environmental samples or portions thereof. A sample may need minimal preparation (for example, collection into a suitable container) for use in a method of the present invention, or more extensive preparation (such as, but not limited to removal, inactivation, or blocking of undesirable material or contaminants, filtration, size selection, affinity purification, cell lysis or tissue digestion, concentration, or dilution). The sample may be in any phase (solid, liquid, or gaseous), in solution or in suspension, as long as it may be treated (such as by mechanical disruption, lysis, heating, addition of a solvent, or suspension agent) to permit detection of the construct-compound complex in solution. For example, a sample may be a soil sample, which may be suspended in an aqueous buffer and optionally filtered to remove undesired particulates before introduction of the binding construct.

The Binding Construct

The present invention includes a binding construct. The binding construct includes a recognition portion that can recognize and bind to the compound of interest, and a nucleic acid portion. The recognition portion can be virtually any molecule or combination of molecules capable of recognizing and binding the compound of interest. Such recognition portions can include, without limitation, peptides, polypeptides, mimotopes, antibodies, Fab fragments, nucleic acids, nucleic acid mimics, aptamers, cell surface antigen, carbohydrates, small molecules (such as a small molecule antigen or a ligand for a receptor), inorganic ions or chelates, or a combination thereof. Particularly preferred is a recognition portion capable of monovalent binding to the compound of interest.

In one embodiment, the recognition portion is an antibody, for example, human or other mammalian IgG, $IgG_1$, $IgG_2$, $IgG_3$, $IgG_4$, IgM, IgA, SigA, or IgE, or avian IgY, and in one preferable embodiment, the recognition portion is an antibody fragment. Preparation of antibodies and antibody fragments against a compound of interest is well known in the art. These techniques are described in, for example, *Antibodies, A Laboratory Manual*, (Harlow and Lane) Cold Spring Harbor Laboratory Press (1988), and updated in *Using Antibodies, A Laboratory Manual*, (Harlow and Lane) Cold Spring Harbor Laboratory Press (1999). Where the recognition portion is an antibody or antibody fragment, it can be natural (such as an immunoglobulin isolated from serum), modified (such as a reduced or deglycosylated antibody), recombinant (such as an antibody produced by phage display), or a combination thereof.

The recognition portion can be a natural, modified, or recombinant antibody binding fragment, such as an Fab fragment, or such as a single-chain antibody variable region fragment or ScFv in which the recombinant variable regions of an immunoglobulin's light and heavy chain domains are connected by a linker sequence (Pantoliano et al., (1991) *Biochemistry*, 30:10117-10125). In one embodiment, the recognition portion of the binding construct includes an Fab fragment, capable of monovalent binding to the compound of interest. Fab fragments against the compound of interest can be produced when antibodies against the compound of interest are cleaved by reduction or enzymatic cleavage of the disulfide bridge that holds the heavy chains together, converting an antibody into two separate Fab fragments, each capable of recognizing and binding the compound of interest, and bearing a reactive sulfhydryl or thiol group that can be attached to other molecules, for example, the nucleic acid portion of the binding construct. In one embodiment, a Fab fragment can be directly covalently attached to a nucleic acid portion through the free sulfhydryl of the Fab fragment, thus forming the binding construct. In another embodiment, the Fab fragment can be indirectly covalently attached to the nucleic acid portion of the binding construct through a bi-functional linker capable of specifically binding both said Fab fragment and said nucleic acid portion forming the binding construct. Alternatively, the recognition portion of the present invention can also be attached to the nucleic acid portion via non-covalent means, for example, via an avidin-biotin interaction, a zinc-polyhistidine interaction, an antibody-antigen interaction, an aptamer-peptide interaction, or via other polypeptides capable of binding nucleic acids such as zinc-binding polypeptide domain.

The recognition portion (for example, peptides, mimotopes, antibodies, or aptamers) can include natural molecules, artificial molecules, fusion or chimeric molecules, molecules developed by random or non-random combinatorial synthesis (Dooley and Houghten (1993) *Life Sci.*, 52: 1509-1517; Kramer et al. (1993) *Peptide Res.*, 6:314-319; Folgori et al. (1994) *EMBO J.*, 13:2236-2243; Smith & Petrenko (1997) *Chem. Rev.*, 97:391-410) or by directed evolution methods such as yeast two-hybrid systems, protein fragment complementation assay, phage display, ribosome display, yeast surface display, and bacterial surface display techniques (Crameri and Suter (1993) *Gene*, 137:69-75; Meola et al. (1995) *J. Immunol.*, 154:3162-3172; Georgiou et al. (1997) *Nature Biotechnol.*, 15:29-34; Mössner and Plückthun (2001) *Chimia*, 55:324; B. K. Kay, J. Winter, and J. McCafferty (editors), "Phage Display of Peptides and proteins: A Laboratory Manual", Academic Press, Inc., San Diego, 1996, 344 pp.), or a combination thereof. The recognition portion can be selected for its ability to recognize and bind the compound of interest by any suitable means known in the art, for example, by affinity selection, affinity purification, iterative panning, or surface plasmon resonance technology (Fägerstam et al. (1991) *J. Mol. Recognition*, 3:208-214; Houshmand et al. (1999) *Anal. Biochem.*, 268: 363-370).

The recognition portion of the binding construct may bind to the compound of interest in a monovalent or in a multivalent fashion. In one preferred embodiment, the binding of the recognition portion of the binding construct to the compound of interest is monovalent. Examples of monovalent binding include, but are not limited to, a Fab fragment that monovalently binds to an antigen, a receptor molecule that monovalently binds its ligand, and an aptamer that monovalently binds a peptide. In certain other embodiments, the binding of the recognition portion of the binding construct to the compound of interest may preferably be multivalent, for example, bivalent or trivalent. Multivalency may be desirable, for example, to increase the avidity of the binding between the binding construct and the compound of interest. In some embodiments, the binding of the recognition portion of the binding construct to the compound of interest may be both bivalent and bispecific (that is, the recognition portion may bind to and recognize two separate specific binding sites of the compound of interest). An example of a bivalent, monospecific binding is a dimeric antibody fragment or diabody (Holliger et al. (1993) *Proc. Natl. Acad. Sci. USA*, 90:6444-6448) that is designed to bind monospecifically. An example of a bivalent, bispecific antibody is a diabody that is designed to bind to two distinct binding sites of the compound of interest.

The nucleic acid portion of the binding construct can include any nucleic acid or nucleic acid mimic that is capable of being detected. The nucleic acid that is used as the nucleic acid portion of the binding construct can include any type of nucleic acid, for example DNA or RNA, or a nucleic acid mimic (such as, but not limited to, a peptide nucleic acid), or a combination thereof. In this respect, the nucleic acid portion of the binding construct acts as a marker for detection, for example, for detection through nucleic acid amplification, nucleic acid hybridization, enzymatic signal amplification, detection of a label, or a combination of these detection methods. The nucleic acid of the invention can be single-stranded or double-stranded.

In one preferred embodiment, the binding construct of the present invention includes a nucleic acid portion, wherein the sequence of the nucleic acid portion does not include a sequence that is expected to be found in the sample, and can thereby be reasonably expected to be less easily contaminated by nucleic acid sequences in the sample, but is, however, designed so as to be easily detectable. For example, where the sample is a serum sample from a mammal, the sequence of the nucleic acid portion can include a nucleic acid sequence believed to occur only in higher plants, and thus unlikely to be found in mammalian serum. In another preferred embodiment, the binding construct of the present invention includes a nucleic acid portion, wherein the sequence of the nucleic acid portion does not include a sequence that is believed to occur in nature. In other embodiments, the nucleic acid portion of the invention can include artificially derived sequences (such as sequences arrived at by random or non-random combinatorial approaches) or repetitive sequences, for example, repetitive sequences that may be complementary to a single hybridization primer or probe. In other embodiments, the nucleic acid portion of the invention can include multiple, repetitive nucleic acid portions attached in series or in parallel to the recognition portion.

The nucleic acid portion is preferably sufficiently long enough to be easily detectable by the detection method chosen. Where detection of the nucleic acid portion includes nucleic acid amplification, the nucleic acid portion preferably includes a single-strand length of between about 50 to about 5000 nucleotides, or between about 100 to about 4000 nucleotides, or between about 200 and about 3000 nucleotides. However, the nucleic acid portion may include any number of nucleotides that is suitable to the chosen method of amplification of the nucleic acid portion, for example PCR or reverse-transcriptase PCR. Where detection of the nucleic acid portion does not include nucleic acid amplification, the nucleic acid portion preferably includes a single strand length of between about 4 nucleotides to about 5000 nucleotides, or between about 20 nucleotides to about 4000 nucleotides, or between about 100 nucleotides to about 3000 nucleotides. However, the nucleic acid portion may include any number of nucleotides that is suitable to the chosen method of detection of the nucleic acid portion.

The recognition portion can be attached to the nucleic acid portion by any method, covalently or non-covalently, directly or indirectly, depending on the nature of a given recognition portion and nucleic acid portion. Such attaching methods can be, for example, covalent cross-linking as well as non-covalent linking methods such as are known in the art (see, for example, R. P. Haugland, "Handbook of Fluorescent Probes and Research Products", 9$^{th}$ edition, J. Gregory (editor), Molecular Probes, Inc., Eugene, Oreg., USA, 2002, 966 pp.; Seitz and Kohler (2001), *Chemistry*, 7:3911-3925; and Pierce Technical Handbook, Pierce Biotechnology, Inc., 1994, Rockford, Ill.). Where desired, for example, when increased flexibility is needed, a recognition portion may be affixed to the nucleic acid portion using a spacer arm. (Keyes et al. (1997) *Biophys. J.*, 72:282-90; Hustedt et al. (1995) *Biochemistry*, 34:4369-4375; and Pierce Technical Handbook, Pierce Biotechnology, Inc., 1994, Rockford, Ill.). In one embodiment, the recognition portion is attached to the nucleic acid portion via covalent linkage. Covalent means are well known in the art and may include, for example, the use of reactive groups, chemical modification or activation, photoactivated cross-linking, or bifunctional or trifunctional cross-linking agents (*Pierce Technical Handbook*, Pierce Biotechnology, Inc., 1994, Rockford, Ill.). In another embodiment, the recognition portion is attached to the nucleic acid portion via non-covalent means. Non-covalent means include, but are not limited to, physical adsorption, electrostatic forces, ionic interactions, hydrogen bonding, hydrophilic-hydrophobic interactions, van der Waals forces, and magnetic forces. A combination of covalent and non-covalent attachment means may be used. For example, the nucleic acid portion (or repetitive multiples of the nucleic acid portion) may be biotinylated and non-covalently attached to a multivalent avidin moiety that is covalently cross-linked to the recognition portion.

The Surfaces and Accessible Binding Targets

The present invention also includes one or more surfaces that bears one or more accessible binding targets that are known to be recognized by and bind to the recognition portion of the binding construct. Such surfaces can be particulate surfaces or non-particulate surfaces, and can be made of any suitable material, such as, but not limited to, plastics, polymers, ceramics, glass, silica compounds, modified silica compounds, fluorocarbons, metals or metal oxides, sorbents, resins, biological materials (for example, polypeptides and carbohydrates), or a combination thereof. Particulate surfaces can be any particle capable of being separated from a liquid sample, for example, magnetic particles, polymeric particles, glass particles, silica particles, ceramic particles, and the like. Particulate surfaces can be any shape including spherical, non-spherical, symmetric, asymmetric, or irregular; they can be of uniform or non-uniform size. Particulate surfaces can take any suitable form, for example, powders, beads, fibers, macromolecular aggregates, nanoparticles, or nanotubes. Particulate surfaces may be optionally enclosed in a chamber, such as in a reusable or a disposable cartridge, cassette, or insert. Non-particulate surfaces include but are not limited to planar or non-planar surfaces (for example, the sides of a tube or a well), non-porous films or membranes, porous films or membranes, fibers, fillers, meshes, grids, filters, matrices, gels, or a combination thereof.

The accessible binding targets of the present invention can be any binding target capable of being recognized by and binding to the recognition portion of the binding construct, for example, nucleic acids, peptide mimotopes or epitope mimetics for antibody variable regions (Geysen et al. (1986) *Mol. Immunol.*, 23:709-715), proteins, glycoproteins, lipoproteins, lectins, antibodies, enzymes, receptors; carbohydrates (monosaccharides, oligosaccharides, and polysaccharides) and glycosylated molecules; lipids, fats, and lipidated molecules; and whole or partial antigens; small molecules (for example, ligands for a receptor, drugs of abuse, inorganic ions or chelates, metabolites, chemical intermediates, or natural products). Accessible binding targets may be monomers, oligomers, polymers; they can also be multi-molecular assemblies. Accessible binding targets may be of completely natural origin, completely artificial origin, or a combination of both (such as a compound of natural origin that is chemically modified).

The accessible binding target can be attached to the surface by any method, covalent or non-covalent, directly or indirectly, depending on the nature of a given surface and accessible binding target. The accessible binding target can be attached to the surfaces by covalent bonds, for example, through the reaction of a chemically reactive group of the accessible binding target with a chemically reactive group of the surface, using appropriate reagents. For example, binding targets bearing primary amines can be linked to amine-binding supports to form a secondary amine using sodium cyanoborohydride; binding targets bearing carbohydrates can be linked to surfaces bearing a free hydrazide group to form a stable hydrazone bond. In another example, 1-ethyl-3[3-dimethylaminopropyl]-carbodiimide hydrochloride (EDC) can be used to link carboxyl groups to surfaces bearing primary amines. The accessible binding target can be attached to the surface by non-covalent means, including, but not limited, to physical adsorption, electrostatic forces, ionic interactions, hydrogen bonding, hydrophilic-hydrophobic interactions, van der Waals forces, and magnetic forces. Non-limiting examples of non-covalent means include biotin-avidin interactions, protein A or protein G interactions with immunoglobulins, and antigen-antibody interactions.

The accessible binding target may be covalently attached to surfaces, such as, but not limited to, polymeric, ceramic, glass, silica, or organic surfaces, through a variety of surface chemistries. Surfaces, both particulate and non-particulate, are readily available with carboxyl, amino, hydroxyl, hydrazide, or chloromethyl functional groups. In one embodiment, where the surface is a magnetic particle, commercial magnetic stocks may be used, and may be selected for properties allowing the desired accessible binding target to be attached to the magnetic particles. For example, the commercially available magnetic particle stock Micromod, Nanomag Silica™, NH250 (catalogue number 13-01-252, Micromod Partikeltechnologie GmbH, Rostock-Warnemuende, Germany) contains on its surface a free amino group, which can be reacted with cross linkers, for example, N-succinimidyl(4-iodoacetyl)aminobenzoate (SIAB) or sulfosuccinimidyl-4-(N-maleimindomethyl)cyclohexane-1-carboxylate (Sulfo-SMCC), each of which has an amine-reactive end and a sulfhydryl-reactive end. The NSH ester of SIAB can couple to primary amine containing molecules, and the ensuing reaction is a stable amide linkage.

Separation

The construct-surface and any excess unbound surfaces are separated from the construct-compound complexes in the sample solution using any suitable method of separation, which can depend on the type of surface used. Such methods can include, without limitation, separation by pressure or vacuum, centrifugation, size-exclusion, filtration, or a combination thereof. The following are non-limiting examples of separation. Where the surfaces are particulates (such as powders, beads, fibers, macromolecular aggregates, nanoparticles, or nanotubes), the construct-surface complexes can be separated by sedimentation, centrifugation, filtration, size-exclusion, or non-covalent attraction (for example, charge or hydrophobicity interaction). Where the surfaces are planar or non-planar non-particulates (such as the walls of a microtiter well or a tube or vessel), the construct-surface complexes can be separated by decanting or aspiration. Where the surfaces are magnetic particles, separation of the construct-surface complexes from the mixture may be accomplished by application of magnetic force, such as by exposure to a magnet.

In one embodiment, the surfaces can be enclosed, permanently or temporarily, in a chamber (such as in a tube, cartridge, column, or cassette), which can facilitate separation of the excess or unbound binding construct. For example, the mixture containing the sample and binding construct can be passed through a cartridge or column containing accessible binding targets bound to surfaces (such as beads, a matrix, a gel, or a filter), whereby the solution that is eluted or that passes through the cartridge or column is stripped of excess or unbound binding construct.

In some embodiments, "separation" of the construct-surface complexes from the mixture need not require physical removal of the construct-surface complexes from the solution, where it is sufficient to isolate the construct-surface complexes from the solution-phase detection step. For example, where the surfaces are magnetic particles, adequate separation of the construct-surface complexes from the mixture may be accomplished by application of magnetic force, for example, to the side of a vessel containing the mixture, thus attracting the magnetic particles to the side of the vessel and isolating them from the solution, allowing an aliquot of the solution to be sampled for the detection step.

In an alternative embodiment, any binding construct not bound to a compound of interest in a construct-compound complex can be separated from the solution by methods such as, but not limited to, precipitation, "salting-out", size-exclusion or filtration, extraction, or phase-separation. In this alternative embodiment, the principles of the methods of the invention remain the same, that is to say, (1) the use of only a single binding entity (the binding construct); (2) the separation of substantially all binding constructs not bound to a compound of interest, resulting in an increased proportion of true "positive" signal to false "positive" signal, and therefore an increased sensitivity of detection of the compound of interest; (3) detection in solution phase, and no requirement for solid-phase detection; and (4) no requirement for prior knowledge of a nucleic acid sequence of the compound of interest.

Detection

After the separation step, by detecting the presence or absence of the nucleic acid portion of the binding construct, the presence or absence of the compound of interest in the sample is indicated. The presence or absence of the nucleic acid portion of the binding construct can be detected by any method, not necessarily involving nucleic acid amplification, that is capable of detecting the presence or absence of nucleic acid, for example, enzymatic amplification, hybridization, or detection of a label. The detection of the nucleic acid portion of the binding construct can be accomplished by any method suitable for such purpose. These methods are well known in the art and they include, without limitation, amplification of the nucleic acid portion, hybridization of the nucleic acid portion, amplification of a signal, detection of a label, or a combination thereof.

Methods of the present invention can include nucleic acid amplification of the nucleic acid portion. Preferred embodiments of the present invention are capable of detecting low amounts or concentrations of the compound of interest, and are capable of amplifying and detecting a few, and a minimum of one, construct-compound complexes. In such preferred embodiments, only a few, and a minimum of one, construct-compound complexes need be remain in solution to serve as amplification templates after the separation of the construct-surface complexes. The amplified nucleic acid can be measured or detected by any suitable method, for example, using labelled oligonucleotides as hybridization probes or by detecting amplified fragments of the appropriate size by polyacrylamide gel electrophoresis. Amplification of the nucleic acid portion may use any suitable amplification method, such as polymerase chain reaction amplification or reverse transcriptase amplification (Molecular Cloning: A Laboratory Manual, Joseph Sambrook et al., Cold Spring Harbor Laboratory, 2001, 999 pp.; Short Protocols in Molecular Biology, Frederick M. Ausubel et al. (editors), John Wiley & Sons, 2002, 1548 pp.), rolling circle amplification (Liu et al. (1996), *J. Am. Chem. Soc.,* 118: 1587-1594), antisense RNA amplification (Phillips and Eberwine (1996) *Methods,* 10:283-288), strand displacement amplification (Walker et al. (1992), *Nucleic Acids Res.,* 20:1691-1696), composite primer/strand displacement amplification (U.S. Pat. No. 6,251,639 to Kurn, "Methods and compositions for linear isothermal amplification of polynucleotide sequences, using a RNA-DNA composite primer", issued Jun. 26, 2001), Q-beta replicase-mediated amplification (Lomeli et al. (1989) *Clin. Chem.,* 35:1826-1831), linked linear amplification (Reyes et al. (2001) *Clin. Chem.,* 47:31-40), self-sustained sequence replication (3SR) (Fahy et al. (1991) *Genome Res.,* 1:25-33), or other nucleic acid amplification methods known in the art (Andras et al. (2001) *Mol. Biotechnol.,* 19:29-44). Another method of detection of the nucleic acid portion of the binding construct can be, for example, by primer extension and detection of the extended nucleic acid.

Hybridization of the nucleic acid portion may be achieved by hybridization of a probe to the nucleic acid portion of the binding construct, followed by detection of the hybridized structure, according to methods known in the art. The probe may include DNA, RNA, a nucleic acid mimic (such as, but not limited to, a peptide nucleic acid), or a combination thereof. The probe may include a suitable detectable label, such as, but not limited to, radioisotopes, spin labels, fluorophores (including organic dyes and lanthanide chelates), chromophores, one or both members of a resonance energy transfer pair, haptens, antigens, antibodies, or enzymes. A label, for example, a fluorophore or a hapten, can also be incorporated directly into the nucleic acid by methods known in the art followed by the detection of the label. Detection of the nucleic acid may include enzymatic amplification of a signal (such as a signal from a label on a probe), for example by using peroxidase-tyramide signal amplification (R. P. Haugland, "Handbook of Fluorescent Probes and Research Products", 9$^{th}$ edition, J. Gregory (editor), Molecular Probes, Inc., Eugene, Oreg., USA, 2002, 966 pp.) or alkaline phosphatase-anti-alkaline phosphatase signal amplification. The nucleic acid portion of the binding construct can also be detected, directly or after amplification or hybridization, by other methods, including but not limited to molecular beacons (optionally combined with real time detection) or other resonance energy transfer methods, or immunological detection (for example, using antibodies that recognize and capture an amplified DNA sequence in an ELISA-type assay).

When detection of the nucleic acid portion of the binding construct involves amplification, a preferred method is amplification of the nucleic acid portion by polymerase chain reaction, according to methods known in the art (Molecular Cloning: A Laboratory Manual, Joseph Sambrook et al., Cold Spring Harbor Laboratory, 2001; Short Protocols in Molecular Biology, Frederick M. Ausubel et al. (editors), John Wiley & Sons, 2002). The capability to detect a compound of interest in a sample can be significantly increased and broadened by coupling to polymerase chain reaction. PCR allows for enormous amplification capability and is a process where a specific sequence of nucleic acid can be amplified millions of times. This enormous amplification capability is based on the ability to amplify a specific target sequence of nucleic acid flanked by a set of primers.

Once the nucleic acid is amplified, the result can be detected using any method suitable for such purpose, for example, using an agarose gel.

EXAMPLES

Example I

A Non-Limiting Embodiment of a Method for Detection of a Compound of Interest in a Sample FIG. 1 depicts a plurality of binding constructs for use in a method of the present invention, as described in Example III. Each binding construct 101 includes a recognition portion 102, which recognizes and binds the compound of interest, and a nucleic acid portion 103. In this embodiment, the recognition portion 102 preferably includes a Fab fragment, such as a Fab fragment made by cleaving the disulfide bridge of the heavy chains of a monoclonal antibody against the compound of interest. In this embodiment, the nucleic acid portion 103 preferably includes DNA. The recognition portion 102 can be attached to the nucleic acid portion 103 through a covalent bond 104, for example, through a covalent bond between the nucleic acid portion 103 and the free sulfhydryl of the Fab fragment of the recognition portion 102.

Figure 2:
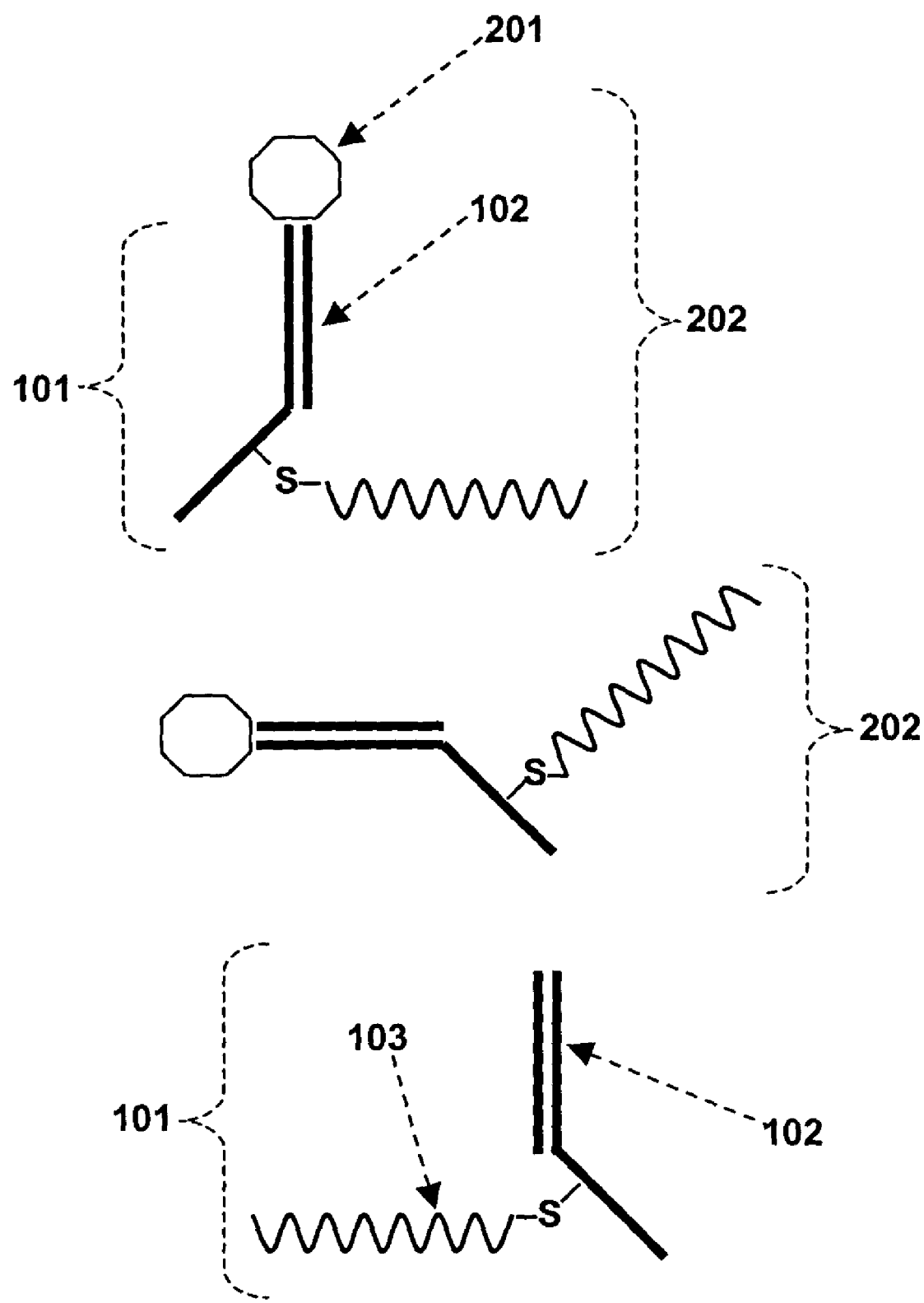
FIG. 2 depicts a plurality of binding constructs, some of which have recognized and bound a compound of interest to their recognition portion to form a construct-compound complex (see Example I).

FIG. 2 shows a number of binding constructs 101 that have been mixed with a sample containing a compound of interest 201, as described in Example IV. The recognition portion 102 of the binding construct 101 has recognized a compound of interest 201 forming a construct-compound complex 202. Also shown in the lowest part of the figure is a binding construct 101, including a recognition portion 102, which has not bound the compound of interest 201, and a nucleic acid portion 103.

Figure 3:
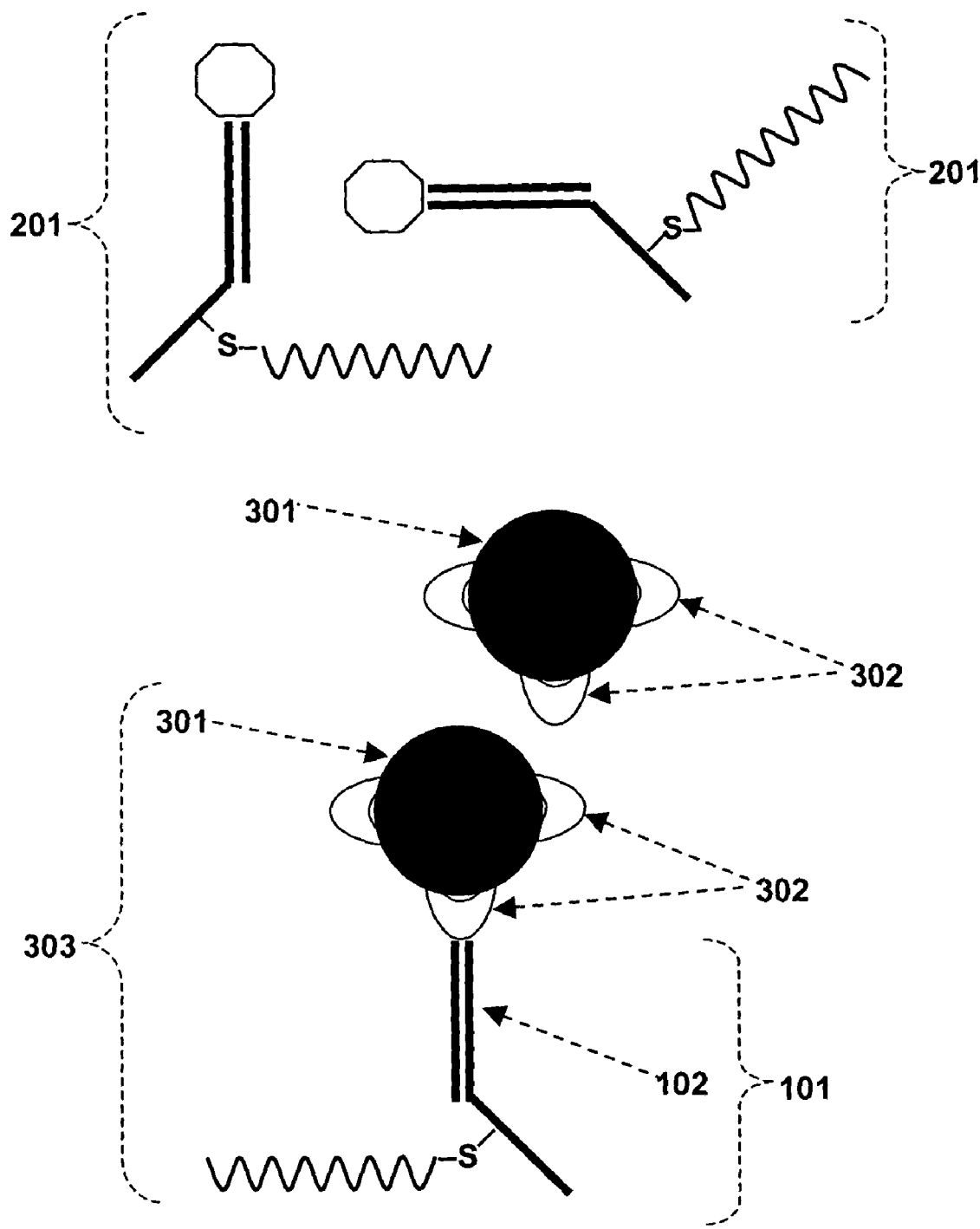
FIG. 3 depicts the surfaces bearing accessible binding targets, which are recognized by and are bound to the recognition portion of the binding constructs forming construct-surface complexes (see Example I).

FIG. 3 shows surfaces 301, bearing accessible binding targets 302. In this embodiment, the surfaces 301 are magnetic particles and the accessible binding targets 302 are peptide mimotopes, as described in Example II. The surfaces are introduced to the sample mixture, which can contain binding constructs 101, which may be bound to a compound of interest in a construct-compound complex 201, or not bound to a compound of interest. The accessible binding target 301 binds to the recognition portion 102 of any binding construct 101 not bound to a compound of interest, forming a construct-surface complex 303.

Figure 4:
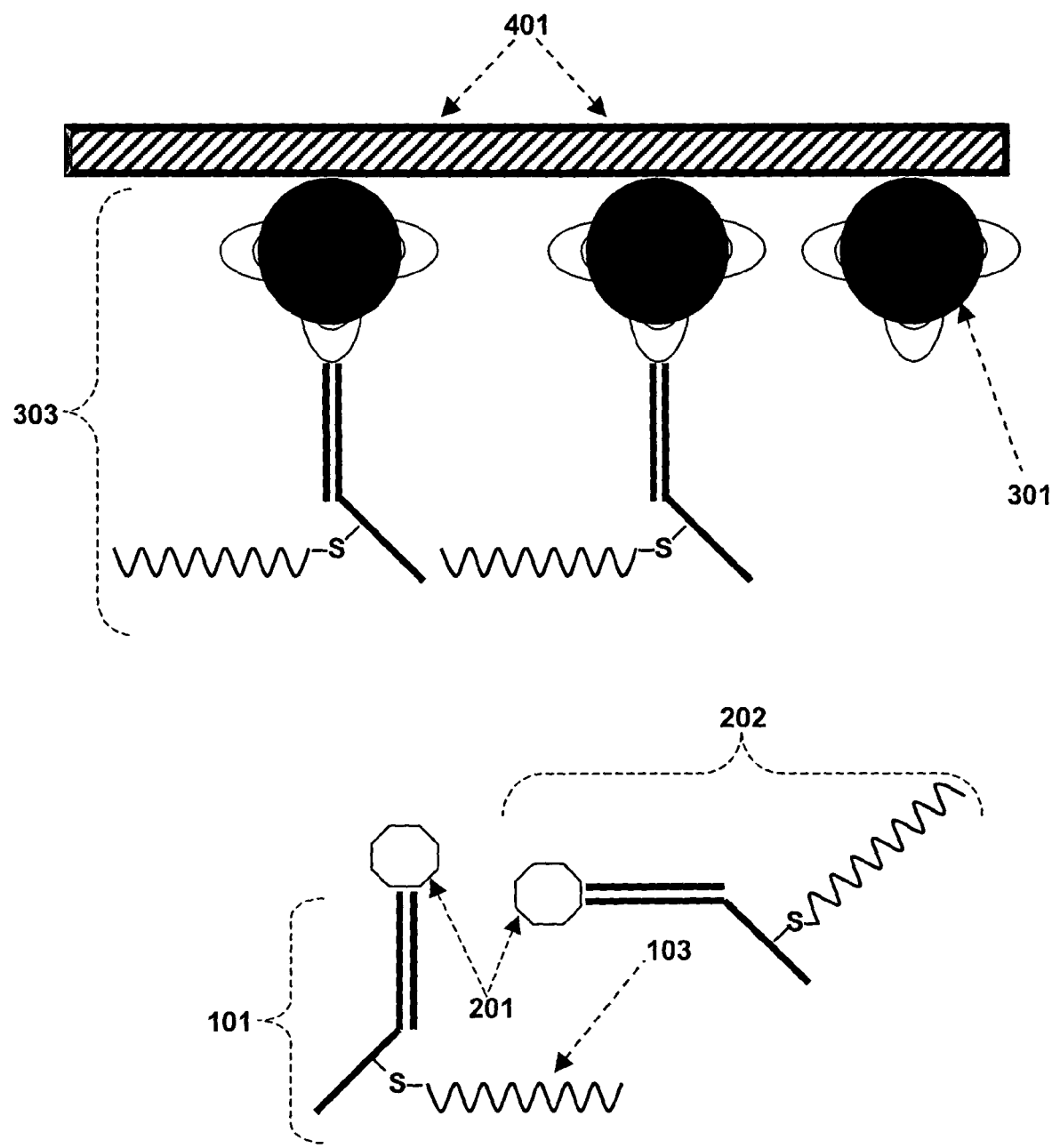
FIG. 4 depicts separation of the construct-surface complexes from the construct-compound complexes (see Example I).

FIG. 4 shows a magnet 401 being used to separate the construct-surface complexes 303, as described in Example IV. The construct-surface complexes 303 and any excess or unbound surfaces 301 are separated, leaving the construct-compound complexes 202 in solution. After separation, the nucleic acid portion 103 of the binding construct 101 included in a construct-compound complex 202 can be detected by any method suitable for that purpose. Detecting the presence of the nucleic acid portion 103 of the binding construct 101 indicates the presence of the compound of interest 201.

Example II

Preparation of the Magnetic Particles Bearing Mimotopes

This example provides one non-limiting embodiment of the present invention wherein the surfaces are magnetic particles bearing peptide mimotopes as the accessible binding targets. In this model system, an antibody that recognizes a bacterial cell wall protein, the *Moraxella catarrhalis* OMPE protein, was used. A bacterial recombinant fragment of *M. catarrhalis* OMPE protein was provided by Dr. Timothy Murphy at the University of Buffalo and used as the immunogen for preparing monoclonal antibody 12D.5 (Mab 12D.5). Using overlapping peptide mapping, the antigenic epitope was shown to reside within amino acids 187-220 of the recombinant fragment. A peptide corresponding to this epitope, designated Mopep2, was synthesized with an N-terminal cysteine for post-synthesis attachment to free sulfhydryl-binding structures. Mab 12D.5 was cleaved into two Fab fragments using 2-mercaptoethylamine HCL (Pierce) leaving a reactive sulfhydryl group that can be attached to another molecule.

Ten milligrams per milliliter of magnetic particle stock Micromod, Nanomag Silica™, NH250, (lot number 210213T, catalogue number 13-01-252, Micromod Partikeltechnologie GmbH, Rostock-Warnemuende, Germany), which contains a free amino group on its surface, was reacted with 140 micrograms SIAB in DMSO and rotated in the dark for 2 hours. The particles were separated by means of a magnet and subsequently incubated in 50 millimolar sodium borate buffer pH 9.6 containing 5 millimolar EDTA with 100 microliter of 1.7 milligrams per milliliter Mopep2 in DMSO and incubated overnight. The free sulfhlydryl group on the Mopep2 peptide was reacted with the SIAB-treated magnetic particles creating a stable thioether bond. Unreacted sites were blocked with free cysteine and the Mopep2-labelled particles were washed and resuspended in 1 milliliter PBS for analysis.

Figure 5:
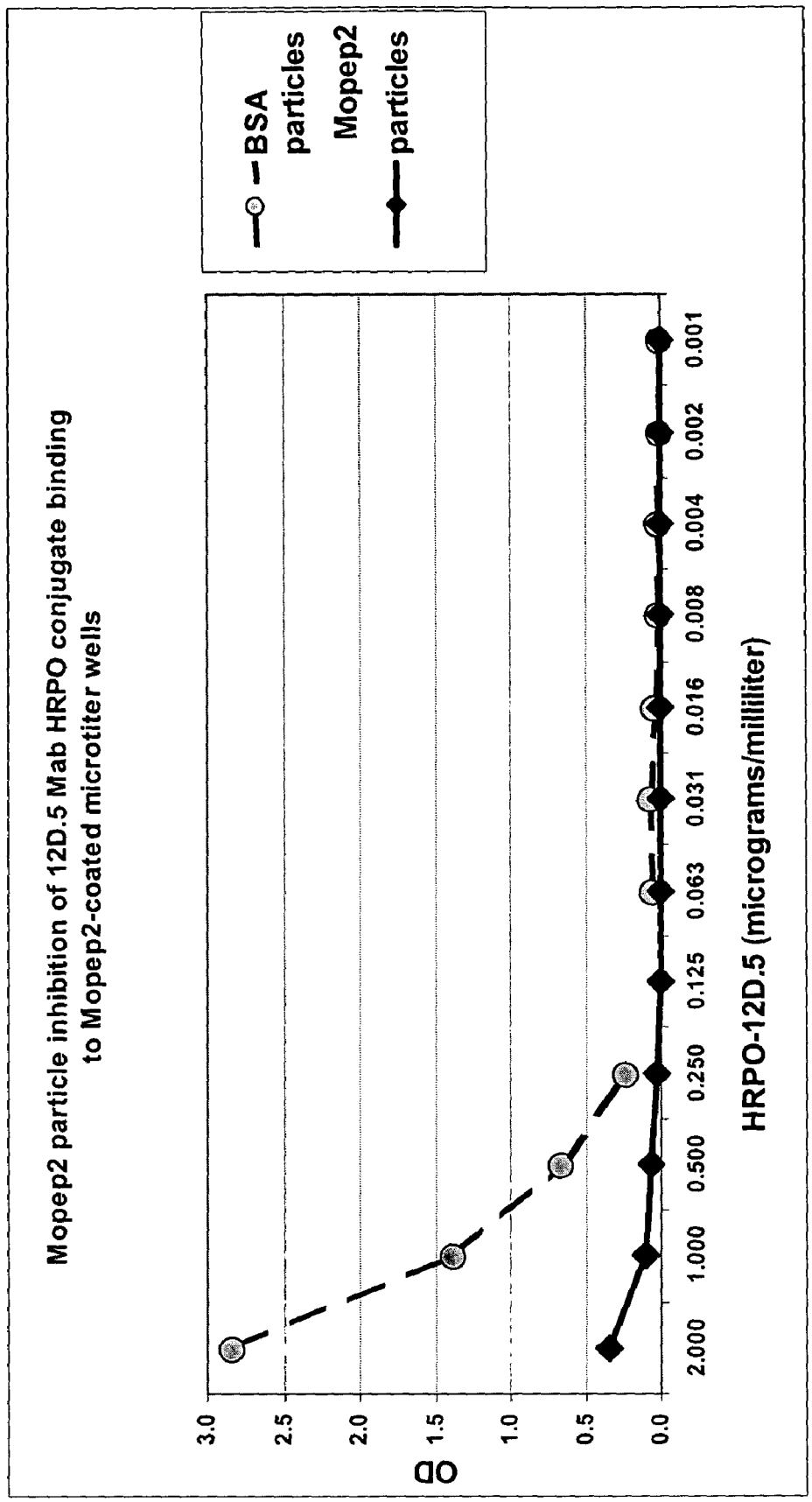
FIG. 5 depicts results of Example II: The Mopep2 particles were capable of binding to and separating monoclonal antibody 12D5 (12D.5 Mab) horseradish peroxidase (HRPO) conjugates from solution, thus preventing the 12D.5 Mab HRPO conjugate from binding to Mopep2-coated wells in a dose-dependent manner. Particles coated with bovine serum albumin (BSA) were unable to inhibit 12D.5 Mab HRPO conjugate from binding to Mopep2-coated wells. OD, optical density.

To test the ability of the Mopep2 particles to bind to free 12D.5 Mab in solution, an inhibition ELISA was performed. Ten microliters of either Mopep2-particles or control particles similarly labelled with bovine serum albumin (BSA) were incubated with a 2-fold serial dilution of horseradish peroxidase (HRPO)-conjugated 12D.5 in PBS (total volume 100 microliters) starting at 2 microgram/millilitre in a 96-well microtiter plate and incubated for 30 minutes. Particles were separated to the bottom of the wells by means of a magnet and 50 microliters of each dilution set were added to Mopep2-coated plates and incubated for an additional 30 minutes. A standard ELISA was then performed with the addition of 3,3'5,5'-tetramethylbenzidine substrate, allowed to develop for 10 minutes, and absorbance read at 630 nanometers with no stop solution added. Data depicted in FIG. 5 show that the Mopep2 particles were capable of binding to and separating monoclonal antibody 12D5 (12D.5 Mab) horseradish peroxidase (HRPO) conjugates from solution, thus preventing the 12D.5 Mab HRPO conjugate from binding to Mopep2-coated wells in a dose-dependent manner. Particles coated with bovine serum albumin (BSA) were unable to inhibit 12D.5 Mab HRPO conjugate from binding to Mopep2-coated wells.

Example III

Preparation of the Binding Construct

This example provides one embodiment of the binding construct in which an Fab fragment is used as the recognition portion of the binding construct. The plasmid pUC 19 was purchased from Invitrogen and plasmid DNA was linearized by EcoRI. The linearized pUC19 DNA was extracted and purified from agarose gel. This DNA was attached to the Fab fragment of Mab 12D.5 and served as the nucleic acid portion of the binding construct. Commercially available primers were subsequently used to amplify a 1 kilobase fragment from the linearized pUC19 template. To generate a DNA fragment that would be attached to the 12D.5 Fab fragment through the free sulfhydryls (—SH) and serve as the nucleic acid portion of the binding construct, a 5'-psoralen, 3'-amino oligonucleotide was conjugated to a SIAB linker through the available amine. The pUC 1 kilobase DNA was denatured in the presence of excess oligonucleotide and snap annealed to the psoralen using long wave ultraviolet light. The excess oligonucleotide was removed with an molecular weight cut-off (MWCO) filter and the SIAB/pUC template was then attached to the Fab fragment using the free sulfhydryl-binding end of the attached linker. The entire binding construct, designated Fab-DNA, was not further purified.

Example IV

Detection of a Compound of Interest by PCR

This example provides one embodiment for detection of a compound of interest wherein the nucleic acid portion of the binding construct is amplified by PCR. This experiment demonstrated the ability of the Fab-DNA binding construct (Mab 12D.5/pUC19 construct) to bind to the compound of interest, the free antigen (bacterial recombinant fragment of OMPE or rOMPE), thus forming construct-compound complexes in solution. Surfaces (magnetic particles) bearing accessible binding targets (Mopep2 peptides) bound any Fab-DNA not bound to the compound of interest, and a magnet was used to separate the surfaces, leaving the construct-compound complexes (Fab-DNA bound to antigen) in solution with the nucleic acid portion (pUC19) of the binding construct available for nucleic acid amplification.

rOMPE was titered in two-fold dilution steps in 1 milliliter PBS from 100 nanograms/millilitre to 1.56 nanograms/millilitre. Each serial dilution was incubated with 20 microliters (8 micrograms of Fab-DNA) for 30 minutes, and then 10 microliters of Mopep2 particles was added to each well and incubated for an additional 30 minutes. Control wells included: (1) 1.1 milliliter PBS and 0.2 milliliter Fab-DNA no rOMPE (positive control), and (2) 1 milliliter PBS, 0.2 milliliter Fab-DNA, and 0.1 milliliter particles (negative control). Wells were exposed to a rare earth magnet for 15 minutes to separate the magnetic particles from the solution, and 0.2 milliliter of the solution removed from each well for amplification.

Samples were amplified by PCR as follows. A 50 microliter PCR reaction mix contained 5 microliters 10×PCR buffer without MgCl$_2$, 1 microliter of 50 millimolar MgCl$_2$, 0.5 microliter of 50 millimolar dNTPs, 1 microliter of each sense or antisense primer to pUC19, 1 microliter Taq polymerase, 2 microliters of sample (solution), and 38.5 microliters ddH$_2$O. The sense primer had the sequence CCTCTAGAGTCGACCTGCAGGCATGC (SEQ ID NO. 1). The anti-sense primer had the sequence CACTGGCCGTCGTTTFACAACGTCGTG (SEQ ID) NO. 2). All sequences are given in the 5' to 3' direction.

Samples were amplified using the following cycling parameters:

| STEP | TIME | TEMPERATURE | CYCLES |
| --- | --- | --- | --- |
| Initial denaturation | 2 minutes | 93° C. | 1 |
| Denaturation | 30 seconds | 93° C. | 35 |

-continued

| STEP | TIME | TEMPERATURE | CYCLES |
|---|---|---|---|
| Annealing | 30 seconds | 52° C. | 35 |
| Extension | 2 minutes | 73° C. | 35 |
| Final extension | 7 minutes | 73° C. | 1 |

Figure 6:
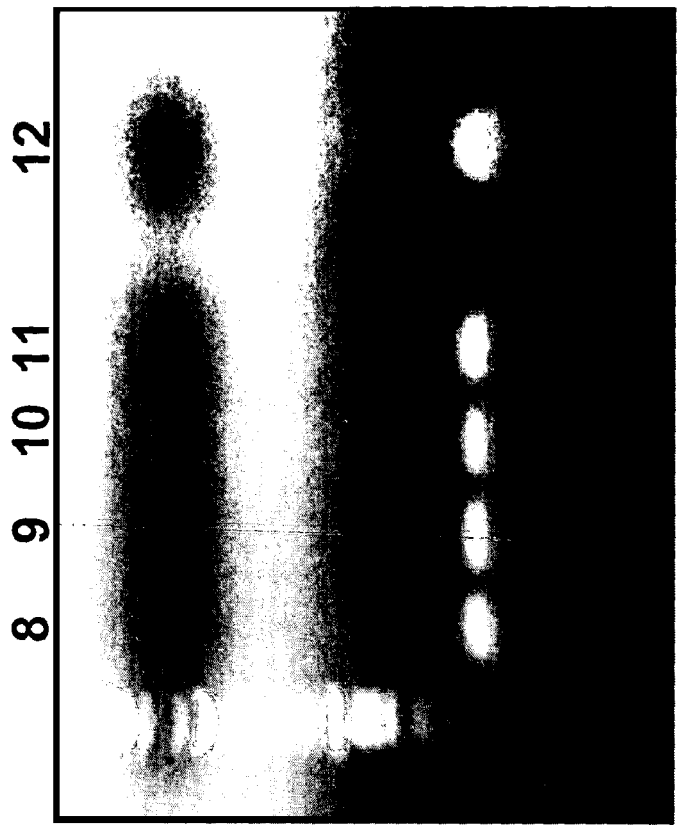
FIG. 6 depicts the results obtained in Example IV, using a method of the invention to detect a compound of interest wherein the nucleic acid portion of the binding construct is amplified by PCR. This experiment demonstrated the ability of the binding construct Fab-DNA (Mab 12D.5/pUC19 construct) to bind to the compound of interest, the free antigen (bacterial recombinant fragment of OMPE or rOMPE), thus forming construct-compound complexes in solution. Surfaces (magnetic particles) bearing accessible binding targets (Mopep2 peptides) bound any Fab-DNA not bound to the compound of interest, and a magnet was used to separate the surfaces, leaving the construct-compound complexes (Fab-DNA bound to antigen) in solution with the nucleic acid portion (pUC19) of the binding construct available for nucleic acid amplification. Polymerase chain reaction amplification resulted in a detectable 2.6 kilobase DNA fragment in the following samples: 790 picogram, 395 picogram, 198 picogram, 98 picogram, and 12 picogram. Very fine 2.6 kilobase bands were also observed in samples of 49 picogram and 24 picogram.
Figure 6:
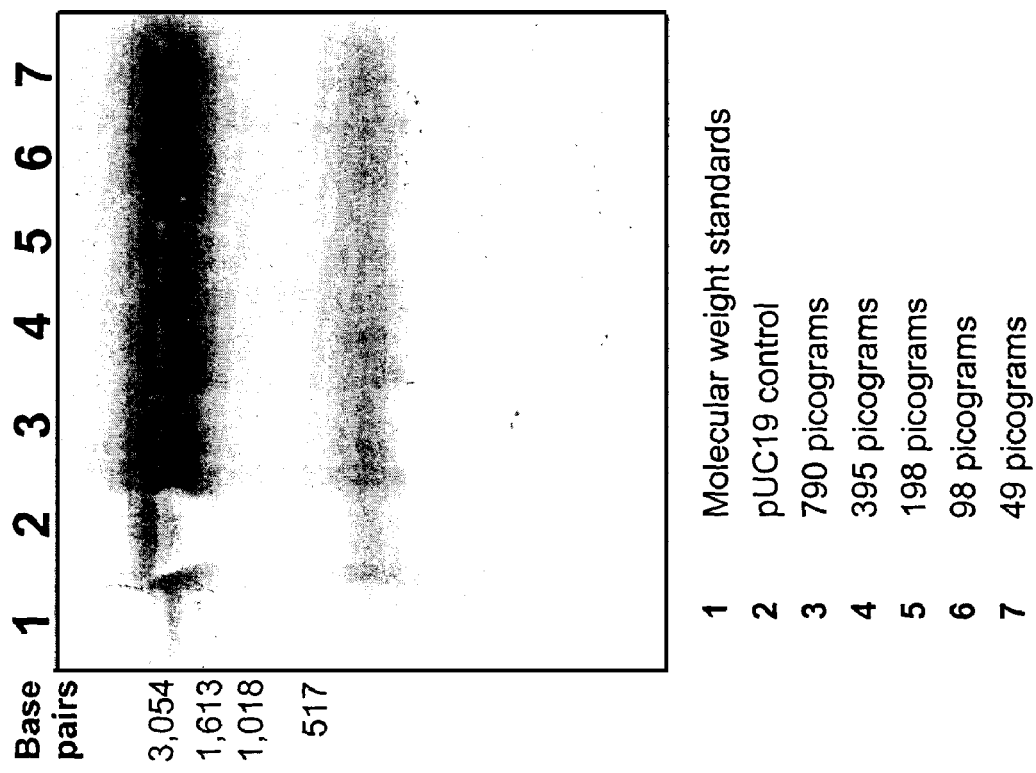

PCR samples were resolved on 1% agarose gel and visualized by ethidium bromide. 10 microliters of each concentration of PCR samples was loaded on the gel. PCR primers amplified an approximate 2650 bp pUC19 fragment. A 1 kilobase extension DNA ladder (Invitrogen) was used as the molecular weight standard. As shown in FIG. 6, PCR primers amplified a 2.6 kilobase DNA fragment in the following samples: 790 picogram, 395 picogram, 198 picogram, 98 picogram, and 12 picogram. Very fine bands were observed in samples of 49 picogram and 24 picogram.

Example V

Detection of Compounds of the Interest

Non-limiting examples of detection of different types of compounds of interest follow.

Beta-Amyloid Protofibrils: In this example, the compound of interest is an oligomer of amyloid beta protein, called a protofibril. Detection of amyloid beta protofibrils can be useful in the early detection of Alzheimer's disease. The sample is serum or cerebral spinal fluid (CSF) from a patient suspected of having or being at risk for Alzheimer's disease. The binding construct includes (1) a recognition portion, which is an antibody or an antibody fragment that recognizes the protofibril, and (2) a nucleic acid portion that does not exist in nature. The nucleic acid portion is a DNA template that can be recognized by synthetic primers designed to bind to the template at low stringency for amplification using PCR. The binding construct is added to a concentration of 10 nanograms per milliliter with a 100 microliter sample of serum, and incubated for a sufficient time to allow the antibody or antibody fragment to bind to protofibrils present in the sample, thus forming construct-compound (construct-protofibril) complexes in solution. The binding surfaces are magnetic particles labelled with an accessible binding target, the same peptide sequence that was used as the immunogen to generate the anti-protofibril antibody (the recognition portion of the binding construct). The magnetic particles bear primary amine reactive groups, allowing the immunogenic peptide to be conjugated to the particles through its carboxy-terminus carboxyl using a water-soluble carbodiimide such as 1-ethyl-3-(3-dimethylaminopropyl)carbodiimide (EDC). Ten microliters of a 30% particle suspension is added to the solution containing construct-compound (construct-protofibril) complexes, allowing the particles to form construct-surface complexes with the unbound anti-protofibril/DNA binding constructs. A magnet is applied to the solution and the magnetic particles are separated, thus separating unbound binding constructs and leaving behind the construct-compound complexes in the solution. Two microliters of the resulting solution (containing construct-compound complexes) are added to a PCR reaction solution containing primers, free nucleotides, and Taq DNA polymerase. The DNA portion of any binding constructs present as construct-compound complexes in solution is amplified. The PCR reaction is resolved on a 1% agarose gel and visualized by ethidium bromide staining. The presence or absence of amyloid beta protofibrils in the sample is indicated by the presence or absence, respectively, in the gel of bands corresponding to the correct molecular weight for the amplified DNA fragment.

*Legionella pneumophilia* Antigen: In this example, the compound of interest is a *Legionella pneumophilia* serogroup 1 carbohydrate antigen. *L. pneumophilia* is the causative agent of the community acquired pneumonia known as Legionnaire's disease, and of Pontiac fever. Serogroup 1 is responsible for the majority of cases of Legionnaire's disease. The sample is preferably a urine sample from a patient suspected of having a *L. pneumophilia* infection. The binding construct includes (1) a recognition portion, which is an antibody or an antibody fragment that recognizes the *L. pneumophilia* serogroup 1 carbohydrate antigen ("antigen"), and (2) a nucleic acid portion that does not exist in nature. The nucleic acid portion is a DNA template that can be recognized by synthetic primers designed to bind to the template at low stringency for amplification using PCR. The binding construct is added to a concentration of 10 nanograms per milliliter with a 100 microliter sample of urine, and incubated for a sufficient time to allow the antibody or antibody fragment to bind to *L. pneumophilia* serogroup 1 carbohydrate antigen present in the sample, thus forming construct-compound (construct-antigen) complexes in solution. The binding surfaces are magnetic particles labelled with an accessible binding target, a peptide mimotope that is capable of binding to the variable regions of the antibody or antibody fragment (the recognition portion of the binding construct). A suitable peptide mimotope can be obtained by methods known in the art, such as phage display of a random or non-random peptide library or combinatorial peptide synthesis, followed by affinity selection (Smith & Petrenko (1997) *Chem. Rev.,* 97:391-410; Kramer et al. (1993) *Peptide Res.,* 6:314-319). The magnetic particles bear primary amine reactive groups, allowing the peptide mimotope to be conjugated to the particles through its carboxy-terminus carboxyl using a water-soluble carbodiimide such as 1-ethyl-3-(3-dimethylaminopropyl)carbodiimide (EDC). Ten microliters of a 30% particle suspension is added to the solution containing construct-compound (construct-*L. pneumophilia* serogroup 1 carbohydrate antigen) complexes, allowing the particles to form construct-surface complexes with the unbound anti-antigen/DNA binding constructs. A magnet is applied to the solution and the magnetic particles are separated, thus separating unbound binding constructs and leaving behind the construct-compound complexes in the solution. Two microliters of the resulting solution (containing construct-compound complexes) are added to a PCR reaction solution containing primers, free nucleotides, and Taq DNA polymerase. The DNA portion of any binding constructs present as construct-compound complexes in solution is amplified. The PCR reaction is resolved on a 1% agarose gel and visualized by ethidium bromide staining. The presence or absence of *L. pneumophilia* serogroup 1 carbohydrate antigen in the sample is indicated by the presence or absence, respectively, in the gel of bands corresponding to the correct molecular weight for the amplified DNA fragment.

*Mycobacterium tuberculosis*-specific Human Antibodies: In this example, the compound of interest is *Mycobacterium tuberculosis*-specific human IgG specific for a 38 kilodalton extracellular protein from *M. tuberculosis* (anti-MTh IgG). *M. tuberculosis* is the causative agent of pulmonary tuberculosis in humans. The sample is preferably serum from a patient suspected of having a *M. tuberculosis* infection. The binding construct includes: (1) a recognition portion, which is a peptide epitope or a mimotope that is recognized and bound by the variable region of the anti-MTh IgG, and (2) a nucleic acid portion, most preferably a nucleic acid portion wherein the sequence of the nucleic acid portion does not include a sequence that is expected to be found in the sample, for example a nucleic acid sequence from higher plants that is not found in either mammals or bacteria. The recognition portion can be a mimotope for the anti-MTb IgG or a native peptide sequence derived from the bacterial protein or peptide that is recognized by the anti-MTh IgG; in either case, the peptide is capable of binding to a subclass of *M. tuberculosis*-specific human immunoglobulin G and forming construct-compound (construct-anti-MTh IgG) complexes. The nucleic acid portion is a DNA template that can be recognized by synthetic primers designed to bind to the template at low stringency for amplification using PCR.

The binding construct is added to a concentration of 10 nanograms per milliliter with a 100 microliter sample of serum, and incubated for a sufficient time to allow the recognition portion of the binding construct to bind to anti-MTh IgG present in the sample, thus forming construct-compound (construct-anti-MTh IgG) complexes in solution. The binding surfaces are agarose beads to which are attached an antibody or antibody fragment that is capable of recognizing and binding to the recognition portion of the binding construct. The agarose beads bear aldehyde reactive groups which may be crosslinked to an amino group on the antibody's heavy chain using sodium cyanoborohydride (NaBH$_3$CN). Twenty microliters of a 30% particle suspension is added to the solution containing construct-compound (construct-anti-MTh IgG) complexes, allowing the beads to form construct-surface complexes with the unbound peptide/DNA binding constructs. The mixture is placed in an Eppendorf tube and centrifuged to pellet the agarose beads out of suspension, leaving the construct-compound (construct-anti-MTh IgG) complexes remaining free in solution in the supernatant. Two microliters of the supernatant solution are added to a PCR reaction solution containing primers, free nucleotides, and Taq DNA polymerase. The DNA portion of any binding constructs present as construct-compound complexes in solution is amplified. The PCR reaction is resolved on a 1% agarose gel and visualized by ethidium bromide staining. The presence or absence of *Mycobacterium tuberculosis*-specific human immunoglobulin G in the sample is indicated by the presence or absence, respectively, in the gel of bands corresponding to the correct molecular weight for the amplified DNA fragment.

All headings are for the convenience of the reader and should not be used to limit the meaning of the text that follows the heading, unless so specified. Various changes and departures may be made to the present invention without departing from the spirit and scope thereof. Accordingly, it is not intended that the invention be limited to that specifically described in the specification or as illustrated in the drawings, but only as set forth in the claims.

What is claimed is:

1. A method for detecting a non-nucleic acid compound of interest in a biological or environmental sample comprising the steps of:

a) providing a binding construct comprising an antibody or an antibody fragment portion which specifically recognizes and specifically binds said non-nucleic acid compound of interest without capture on a solid support, and a nucleic acid portion;

b) mixing said binding construct with said biological or environmental sample in a solution mixture to form construct-compound complexes in solution without capture on a solid support, wherein said non-nucleic acid compound of interest in said biological or environmental sample becomes specifically bound to said binding construct;

c) providing one or more surfaces, wherein said surfaces bear one or more accessible non-nucleic acid binding targets capable of specifically recognizing and specifically binding to said antibody or said antibody fragment portion of said binding construct;

d) introducing said one or more surfaces to said solution mixture of said construct-compound complexes after said non-nucleic acid compound of interest in said biological or environmental sample has become bound to said binding construct in order for said one or more surfaces to form construct-surface complexes in solution with any unbound binding constructs resulting in said solution mixture containing essentially said construct-compound complexes and said construct-surface complexes;

e) separating said construct-surface complexes from said solution mixture leaving behind said construct-compound complexes in solution; and f) detecting the presence or absence of said nucleic acid portion of said construct-compound complexes in solution after said separation step (e), said detection being done without the presence of any of said surfaces in connection with said construct-compound complexes that are being detected;

wherein the presence of said nucleic acid portion of said construct-compound complexes indicates the presence of said non-nucleic acid compound of interest in said biological or environmental sample.

2. The method of claim 1, wherein said one or more surfaces is selected from the group consisting of: particles, powders, beads, planar surfaces, non-planar surfaces, a tube, a well, non-porous films, non-porous membranes, porous films, porous membranes, fibers, fillers, meshes, grids, filters, matrices, gels, and combinations thereof.

3. The method of claim 1, wherein said one or more surfaces comprise particles.

4. The method of claim 3, wherein said particles comprise magnetic particles.

5. The method of claim 4, wherein said step (e) comprises separating said construct-surface complexes out of said mixture by means of a magnet.

6. The method of claim 5, wherein, in step (f), said detecting the presence or absence of said nucleic acid portion of said binding construct comprises amplification of said nucleic acid portion.

7. The method of claim 6, wherein said amplification of said nucleic acid portion comprises a polymerase chain reaction.

8. The method of claim 1, wherein, in step (f), said detecting the presence or absence of said nucleic acid portion of said binding construct comprises amplification of said nucleic acid portion.

9. The method of claim 8, wherein said amplification of said nucleic acid portion comprises a polymerase chain reaction.

10. The method of claim 1, wherein said antibody or antibody fragment portion comprises a single chain antibody variable region fragment.

11. The method of claim 1, wherein said antibody or antibody fragment portion comprises a Fab fragment.

12. The method of claim 11, wherein said Fab fragment is attached to said nucleic acid portion through the free sulfhydryl of the Fab fragment.

13. The method of claim 1, wherein said nucleic acid portion comprises DNA.

14. The method of claim 1, wherein said nucleic acid portion comprises RNA.

15. The method of claim 1, wherein said nucleic acid portion comprises a nucleic sequence that does not include a sequence that is expected to be found in the biological or environmental sample.

16. The method of claim 1, wherein said step (a) comprises providing two or more different types of binding constructs, wherein each of said two or more different binding constructs has a different antibody or antibody fragment portion and a different nucleic acid portion.

17. A method for solution-phase detection of a non-nucleic acid compound of interest, comprising the steps of:
a) providing a biological or environmental sample suspected of containing said non-nucleic acid compound of interest;
b) providing a binding construct comprising:
    i) an antibody or an antibody fragment portion capable of specifically binding said non-nucleic acid compound of interest without capture on a solid support, and
    ii) a nucleic acid portion
c) contacting said biological or environmental sample with said binding construct for a period of time sufficient to permit said antibody or antibody fragment portion to specifically bind said non-nucleic acid compound of interest present in said biological or environmental sample, thereby forming construct-compound complexes in solution, wherein said non-nucleic acid compound of interest in said biological or environmental sample becomes specifically bound to said binding construct;
d) providing one or more surfaces, wherein said one or more surfaces bears one or more accessible non-nucleic acid binding targets capable of specifically binding to said antibody or antibody fragment portion;
e) contacting said one or more surfaces with said solution alter said non-nucleic acid compound of interest in said biological or environmental sample has become bound to said binding construct for a period of time sufficient for said one or more accessible non-nucleic acid binding targets to specifically bind said antibody or antibody fragment portion of any binding construct not bound to said non-nucleic acid compound of interest, thereby forming construct-surface complexes in said solution resulting in said solution containing essentially said construct-compound complexes and said construct-surface complexes;
f) separating said construct-surface complexes from said solution, leaving said construct-compound complexes in said solution; and
g) detecting the presence or absence of said nucleic acid portion of said construct-compound complexes in said solution after said separation step (f), said detection being done without the presence of any said surfaces in connection with said construct-compound complexes that are being detected;
    wherein said separation of said construct-surface complexes from said solution results in a separation of all binding constructs not bound to a non-nucleic acid compound of interest, and
    wherein the presence of said nucleic acid portion of said construct-compound complexes indicates the presence of said non-nucleic acid compound of interest in said biological or environmental sample.

18. The method of claim 17, wherein said one or more surfaces is selected from the group consisting of: particles, powders, beads, planar surfaces, non-planar surfaces, a tube, a well, non-porous films, non-porous membranes, porous films, porous membranes, fibers, fillers, meshes, grids, filters, matrices, gels, and combinations thereof.

19. The method of claim 17, wherein said one or more surfaces comprise particles.

20. The method of claim 19, wherein said particles comprise magnetic particles.

21. The method of claim 20, wherein said step (f) comprises separating substantially all said construct-surface complexes from said solution by means of a magnet.

22. The method of claim 21, wherein, in step (g), said detecting the presence or absence of said nucleic acid portion of said binding construct comprises amplification of said nucleic acid portion.

23. The method of claim 22, wherein said amplification of said nucleic acid portion comprises a polymerase chain reaction.

24. The method of claim 17, wherein, in step (g), said detecting the presence or absence of said nucleic acid portion of said binding construct comprises amplification of said nucleic acid portion.

25. The method of claim 24, wherein said amplification of said nucleic acid portion comprises a polymerase chain reaction.

26. The method of claim 17, wherein said antibody or antibody fragment portion comprises a single chain antibody variable region fragment.

27. The method of claim 17, wherein said antibody or antibody fragment portion comprises a Fab fragment.

28. The method of claim 27, wherein said Fab fragment is attached to said nucleic acid portion through the free sulfhydryl of the Fab fragment.

29. The method of claim 17, wherein said nucleic acid portion comprises DNA.

30. The method of claim 17, wherein said nucleic acid portion comprises RNA.

31. The method of claim 17, wherein said nucleic acid portion comprises a nucleic sequence that does not include a sequence that is expected to be found in said biological or environmental sample.

32. The method of claim 17, wherein said step (b) comprises providing two or more different types of binding constructs, wherein each of said two or more different binding constructs has a different antibody or antibody fragment portion and a different nucleic acid portion.

* * * * *

```
                          SEQUENCE LISTING

<160> NUMBER OF SEQ ID NOS: 2

<210> SEQ ID NO 1
<211> LENGTH: 26
<212> TYPE: DNA
<213> ORGANISM: artificial sequence
<220> FEATURE:
<223> OTHER INFORMATION: synthetic construct

<400> SEQUENCE: 1
cctctagagt cgacctgcag gcatgc                                            26

<210> SEQ ID NO 2
<211> LENGTH: 27
<212> TYPE: DNA
<213> ORGANISM: artificial sequence
<220> FEATURE:
<223> OTHER INFORMATION: synthetic construct

<400> SEQUENCE: 2
cactggccgt cgttttacaa cgtcgtg                                           27
```